United States Patent
Schab et al.

(10) Patent No.: US 9,894,885 B2
(45) Date of Patent: Feb. 20, 2018

(54) MOBILE ANIMAL SURVEILLANCE AND DISTRESS MONITORING

(71) Applicant: Equus Global Holdings LLC, Austin, TX (US)

(72) Inventors: Jeffrey R. Schab, Austin, TX (US); Michael W. Schab, Rochester, NY (US); Ryan M. Bowen, Fairport, NY (US)

(73) Assignee: EQUUS GLOBAL HOLDINGS LLC, Austin, TX (US)

( * ) Notice: Subject to any disclaimer, the term of this patent is extended or adjusted under 35 U.S.C. 154(b) by 0 days.

(21) Appl. No.: 15/494,761

(22) Filed: Apr. 24, 2017

(65) Prior Publication Data

US 2017/0223931 A1 Aug. 10, 2017

Related U.S. Application Data

(63) Continuation of application No. 14/626,740, filed on Feb. 19, 2015, now Pat. No. 9,629,340.

(Continued)

(51) Int. Cl.
*A01K 29/00* (2006.01)
*A61B 5/0205* (2006.01)
(Continued)

(52) U.S. Cl.
CPC .......... *A01K 29/005* (2013.01); *A61B 5/0008* (2013.01); *A61B 5/0022* (2013.01); *A61B 5/0075* (2013.01); *A61B 5/02055* (2013.01); *A61B 5/7203* (2013.01); *A61B 5/7246* (2013.01); *A61B 5/7257* (2013.01); *A61B 5/7264* (2013.01); *A61B 5/7282* (2013.01); *A61B 5/746* (2013.01); *A61B 7/008* (2013.01); *A61D 17/008* (2013.01); *G06N 7/02* (2013.01); *G06N 99/005* (2013.01); *G08B 21/182* (2013.01); *A61B 5/024* (2013.01); *A61B 5/05* (2013.01); *A61B 5/0816* (2013.01);
(Continued)

(58) Field of Classification Search
CPC ... A61B 5/1112; A61B 5/1116; A61B 5/7203; A61B 5/7246; A61B 5/72575; A61B 5/7264; A61B 5/7282; A61B 5/746; A61B 7/008; G08B 21/182; A61D 17/008; G06N 7/02; G06N 99/005
See application file for complete search history.

(56) References Cited

U.S. PATENT DOCUMENTS

2010/0030036 A1* 2/2010 Mottram ................ A01K 11/00
600/301
2012/0041279 A1* 2/2012 Freeman .............. A61B 5/0205
600/301

(Continued)

Primary Examiner — Nader Bolourchi
(74) Attorney, Agent, or Firm — Kirk Dorius

(57) ABSTRACT

A method for remote animal surveillance and distress monitoring includes detecting biometric and behavioral parameters of the animal, identifying novel events based on comparison of detected parameters to predefined parameter values and qualifications; determining whether a composite parameter value exceeds a predefined composite threshold value indicative of possible distress in the animal; and notifying remote caretakers of possible distress in the animal based on the composite value exceeding the predefined composite threshold value.

20 Claims, 39 Drawing Sheets

Related U.S. Application Data

(60) Provisional application No. 62/087,076, filed on Dec. 3, 2014, provisional application No. 61/943,677, filed on Feb. 24, 2014.

(51) Int. Cl.

| | | |
|---|---|---|
| *A61B 5/00* | (2006.01) | |
| *A61B 7/00* | (2006.01) | |
| *A61D 17/00* | (2006.01) | |
| *G06N 7/02* | (2006.01) | |
| *G06N 99/00* | (2010.01) | |
| *G08B 21/18* | (2006.01) | |
| *A61B 5/024* | (2006.01) | |
| *A61B 5/05* | (2006.01) | |
| *A61B 5/08* | (2006.01) | |
| *A61B 5/11* | (2006.01) | |

(52) U.S. Cl.
CPC ............ *A61B 5/1112* (2013.01); *A61B 5/1116* (2013.01); *A61B 2503/40* (2013.01); *A61B 2560/0257* (2013.01); *A61B 2562/0219* (2013.01); *A61B 2562/0223* (2013.01)

(56) References Cited

U.S. PATENT DOCUMENTS

| | | | |
|---|---|---|---|
| 2013/0009993 A1* | 1/2013 | Horseman | G06F 19/3406 345/633 |
| 2013/0245436 A1* | 9/2013 | Tupin, Jr. | A61B 5/0444 600/430 |
| 2014/0288383 A1* | 9/2014 | Barnett | A61B 5/48 600/301 |

* cited by examiner

| | | WATCH |
|---|---|---|
| Behaviors | Flehmen Response (mild) | ≥ 2 events/day (any duration). |
| | Bruxism (mild) | ≥ 2 events/day (any duration). |
| | Flank Watch (mild) | While Standing: ≥ 2 events (+/- biting) over 2 mins; or ≥ 50% increase in # of events vs daily average; or ≥ 100% increase in # of events vs prior 30 mins. While Lying Down: ≥ 1 event (+/- biting) over 5 mins (+/- groaning); or ≥ 50% increase in # of events vs daily average; or ≥ 100% increase in # of events vs prior 30 mins. |
| | Paw (moderate) | ≥ 3 events (≥ 5 secs) without sequential roll(s) over 3 mins; or ≥ 50% increase in # of events (> 5 secs) vs daily average; or ≥ 100% increase in # of events (> 5 secs) vs prior 30 mins. |
| | Spin (moderate) | ≥ 3 events (> 15 secs) without sequential roll(s) over 3 mins; or ≥ 50% increase in # of events (> 5 secs) vs daily average; or ≥ 100% increase in # of events (> 5 secs) vs prior 30 mins. |
| | Kick (moderate) | ≥ 2 events/day (any duration). |
| | Rise/Fall (moderate/severe) | ≥ 3 events within 5 mins (+/- roll); or ≥ 25% increase in # of events vs daily average; or ≥ 25% increase in # of events over prior 30 mins. |
| | Lying Down (moderate/severe) | ≥ 3 hours continuous; or ≥ 25% increase in duration vs daily average. |
| | Roll (severe) | Rolling for ≥ 30 secs with no rise; or ≥ 3 rolls (any duration) over 5 mins with no rise; or ≥ 25% increase in # of rolls vs daily average; or ≥ 25% increase in # of vs prior 30 mins. |
| | No Healthy Shake (severe) | ≥ 2 events/day w/in 30 secs of rising; or ≥ 25% increase in # of events vs daily average. |
| Biologic Functions | Digestive Sounds | ≥ 50% sustained decrease in Db level for ≥ 20 secs; or ≥ 25% sustained increase in Db level for > 20 secs; or ≥ 2 intermittent spikes (any Db level) over 3 mins. |
| Biometrics | Heart Rate | ≤ 30 or ≥ 40 beats/min; or > 15% increase over resting normal for > 1 min; or > 15% decrease over resting normal for > 1 min. |
| | Respiratory Rate | ≤ 8 or ≥ 16 breaths/min; or > 35% increase over resting normal for > 1 min; or > 35% decrease over resting normal for > 1 min. |
| | Temperature | ≤ 98.6 or ≥ 100.4 degrees Fahrenheit; or > 1% increase over resting normal for > 10 mins; or > 1% decrease over resting normal for > 10 mins. |

Fig. 4A

| | | WARNING |
|---|---|---|
| Behaviors | Flehmen Response (mild) | ≥ 2 events (any duration) over 2 mins; or ≥ 250% increase in # of events vs daily average; or ≥ 100% increase in # of events vs prior 30 mins. |
| | Bruxism (mild) | ≥ 2 events (any duration) over 2 mins; or ≥ 250% increase in # of events vs daily average; or ≥ 100% increase in # of events vs prior 30 mins. |
| | Flank Watch (mild) | While Standing: ≥ 3 events (+/- biting) over 3 mins; or ≥ 100% increase in # of events vs daily average; or ≥ 150% increase in # of events vs prior 30 mins. While Standing: ≥ 2 events (+/- biting) over 5 mins (+/- groaning); or ≥ 100% increase in # of events vs daily average; or ≥ 150% increase in # of events vs prior 30 mins. |
| | Paw (moderate) | ≥ 5 events (≥ 5 secs) without sequential roll(s) over 5 mins; or ≥ 100% increase in # of events (> 5 secs) vs daily average; or ≥ 150% increase in # of events (> 5 secs) vs prior 30 mins. |
| | Spin (moderate) | ≥ 5 events (≥ 15 secs) without sequential roll(s) over 5 mins; or ≥ 100% increase in # of events (> 5 secs) vs daily average; or ≥ 150% increase in # of events (> 5 secs) vs prior 30 mins. |
| | Kick (moderate) | ≥ 3 events (any duration) over 3 mins; or ≥ 250% increase in # of events vs daily average; or ≥ 100% increase in # of events vs prior 30 mins. |
| | Rise/Fall (moderate/severe) | ≥ 5 events within 5 mins (+/- roll); or ≥ 50% increase in # of events vs daily average; or ≥ 35% increase in # of events over prior 30 mins. |
| | Lying Down (moderate/severe) | > 4 hours continuous; or ≥ 35% increase in duration vs daily average. |
| | Roll (severe) | Rolling for ≥ 45 secs with no rise; or ≥ 4 rolls (any duration) over 10 mins with no rise; or ≥ 50% increase in # of rolls vs daily average; or ≥ 50% increase in # of vs prior 30 mins. |
| | No Healthy Shake (severe) | ≥ 3 events/day w/in 30 secs of rising; or ≥ 35% increase in # of events vs daily average. |
| Biologic Functions | Digestive Sounds | ≥ 50% sustained decrease in Db level for ≥ 1 min; or ≥ 25% sustained increase in Db level for > 1 min; or ≥ 5 intermittent spikes (any Db level) over 3 mins. |
| Biometrics | Heart Rate | ≤ 20 or ≥ 50 beats/min; or > 40% increase over resting normal for > 1 min; or > 40% decrease over resting normal for > 1 min. |
| | Respiratory Rate | ≤ 6 or ≥ 20 breaths/min; or > 75% increase over resting normal for > 1 min; or > 50% decrease over resting normal for > 1 min. |
| | Temperature | ≤ 98.2 or ≥ 101.2 degrees fahrenheit; or > 2% increase over resting normal for > 10 mins; or > 1.75% decrease over resting normal for > 10 mins. |

Fig. 4B

| | | ALERT |
|---|---|---|
| Behaviors | Flehmen Response (mild) | ≥ 5 events (any duration) over 5 mins; or ≥ 500% increase in # of events vs daily average; or ≥ 200% increase in # of events vs prior 30 mins. |
| | Bruxism (mild) | ≥ 5 events (any duration) over 5 mins; or ≥ 500% increase in # of events vs daily average; or ≥ 200% increase in # of events vs prior 30 mins. |
| | Flank Watch (mild) | While Standing: ≥ 5 events (+/- biting) over 5 mins, or ≥ 200% increase in # of events vs daily average, or ≥ 200% (+/- biting) over 5 mins vs prior 30 mins. While Lying Down: ≥ 3 events (+/- groaning); or ≥ 200% increase in # of events vs daily average, or ≥ 200% increase in # of events vs prior 30 mins. |
| | Paw (moderate) | ≥ 5 events (any duration) with sequential roll(s) over a 5 mins; or ≥ 200% increase in # of events (> 5 secs) vs daily average; or ≥ 200% increase in # of events (> 5 secs) vs prior 30 mins. |
| | Spin (moderate) | ≥ 5 events (any duration) with sequential roll(s) over a 5 mins; or ≥ 200% increase in # of episodes (> 5 secs) vs prior 30 mins. (> 5 secs) vs daily average; or ≥ 200%, increase in # of episodes (> 5 secs) vs prior 30 mins. |
| | Kick (moderate) | ≥ 5 events (any duration) over 5 mins; or ≥ 500% increase in # of events vs daily average; or ≥ 200% increase in # of events vs prior 30 mins. |
| | Rise/Fall (moderate/severe) | ≥ 10 events within 5 mins (+/- roll); or ≥ 100% increase in # of events over prior 30 mins. or ≥ 50% increase in duration vs daily average. |
| | Lying Down (moderate/severe) | ≥ 5 hours continuous, or ≥ 50% increase in duration vs daily average. |
| | Roll (severe) | Rolling for ≥ 60 secs with no rise; or ≥ 5 rolls (any duration) over 20 mins with no rise; or ≥ 100% increase in # of rolls vs daily average, or ≥ 100% increase in # of vs prior 30 mins. |
| | No Healthy Shake (severe) | ≥ 5 events/day w/in 30 secs of rising; or ≥ 50% increase in # of events vs daily average. |
| Biologic Functions | Digestive Sounds | ≥ 50% sustained decrease in Db level for ≥ 3 mins; or ≥ 25% sustained increase in Db level for > 3 mins; or ≥ 10 intermittent spikes (any Db level) over 3 mins. |
| Biometrics | Heart Rate | ≤ 12 or ≥ 60 beats/min; or ≥ 70% increase over resting normal for > 1 min; or > 70% decrease over resting normal for > 1 min. |
| | Respiratory Rate | ≤ 4 or ≥ 30 breaths/min; or ≥ 150% increase over resting normal for > 1 min; or > 65% decrease over resting normal for > 1 min. |
| | Temperature | ≤ 96.0 or ≥ 103.5 degrees Fahrenheit; or ≥ 4% increase over resting normal for > 10 mins; or > 3.5% decrease over resting normal for > 10 mins. |

Fig. 4C

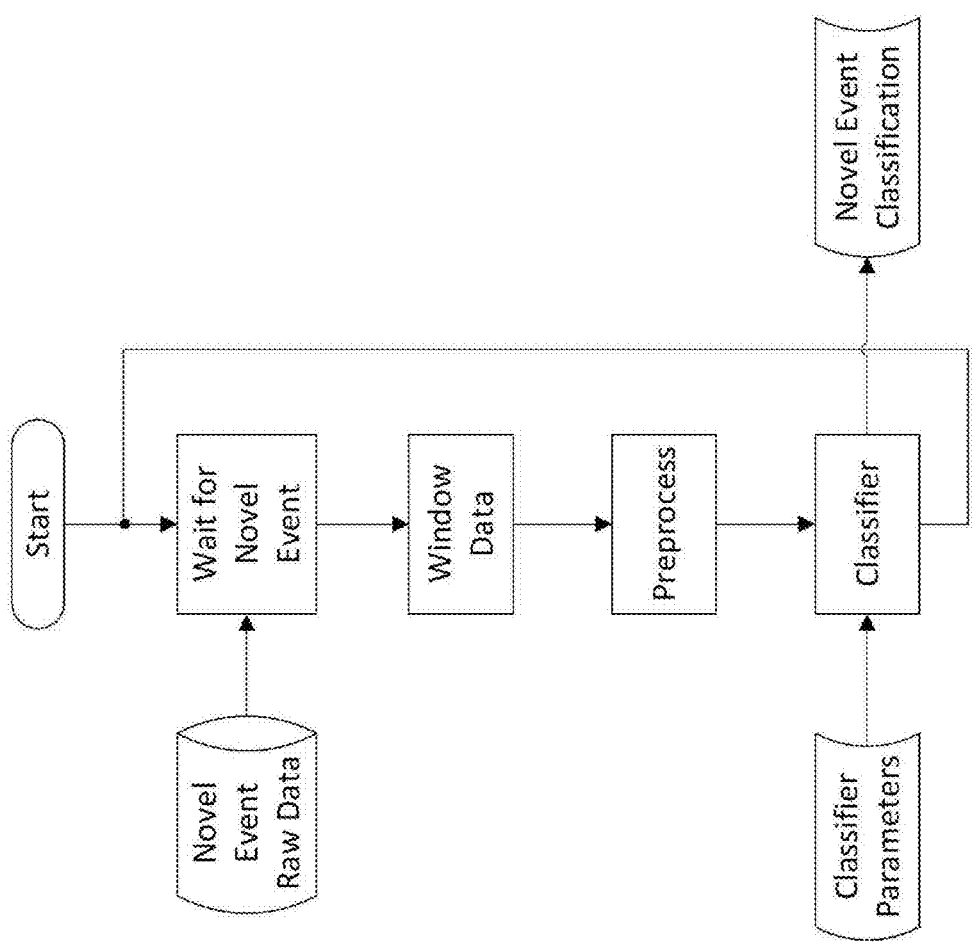

MOBILE ANIMAL SURVEILLANCE AND DISTRESS MONITORING

RELATED APPLICATIONS

This application is a continuation of U.S. application Ser. No. 14/626,740 filed on Feb. 19, 2015 entitled "MOBILE ANIMAL SURVEILLANCE AND DISTRESS MONITORING", which claims priority to U.S. provisional application Ser. No. 61/943,677 filed on Feb. 24, 2014 entitled "System and Method for Mobile Animal Surveillance and Distress Monitoring", and 62/087,076 filed on Dec. 3, 2014 entitled "Method for Mobile Animal Surveillance and Distress Monitoring", all of which are incorporated herein in their entireties by reference.

BACKGROUND OF THE INVENTION

This disclosure relates to detection of animal distress, and particularly to notification of caregivers of such distress. Excluding old age, colic is the leading cause of death in domesticated horses regardless of breed, sex, and usage. It is estimated that this condition afflicts nearly 5% of horses in the US each year and more than 11% of these cases will be fatal. Casting (i.e., stall casting), although seldom traumatic, is another highly-common cause of serious injury to horses. Unfortunately, colic and casting often occur overnight or at remote locations when/where caretakers are not present, resulting in delayed intervention. Delayed intervention is a negative prognostic indicator that has dire impact on survival and quality of life outcomes. Another important time for caregivers to be present is when a mare (i.e., female horse) is about to foal (i.e., give birth). This process occurs very quickly and while more than 90% or mares foal normally, a minority percentage can experience complications that require human intervention to reduce the risk of injury or death to the foal and/or mare.

Colic

Colic is one of the most dangerous and costly equine medical problems. Colic is a symptom of disease, but not a disease itself, and is generally defined as any abdominal pain. Equine colic can involve any number of abdominal organs, not just the gastrointestinal tract. For example, abdominal discomfort from kidney or liver disease will sometimes cause signs of colic. Equine colic can originate from the stomach, small intestine, large intestine, or some combination thereof, and is associated with any malfunction, displacement, twisting, swelling, infection, or lesion of any part of the equine digestive system.

Equine colic is multifaceted and its diagnosis can be elusive with symptoms ranging from subjective and subtle changes in the animal's attitude (e.g., depression) to objective changes in the animal's vital signs (e.g., increased heart and respiratory rates, rise in temperature), biologic functions (e.g., lack of digestion), and actions/movements (e.g., pawing, kicking, flank watching, rising/falling, rolling+/−thrashing). Further, a horse in distress will not usually display a healthy shake upon rising/standing after rolling or lying down. A horse suffering from colic may show any number of the following signs:

Pawing and/or scraping (front legs)
Kicking (back legs) up, or at abdomen
Repeated lying down and rising/standing
Rolling (+/−thrashing)
Stretching
Pacing
Flank watching (i.e., turning of the head to watch stomach and/or hind quarters)
Biting/nipping the stomach
Repeated flehmen response (i.e., curling of upper lip)
Groaning
Bruxism (i.e., excessive grinding of the teeth or clenching of the jaw)
Excess salivation
Loss of appetite
Change in attitude; depression
Frequent attempts to urinate
Lack of normal digestive/gut noise
Lack of defecation
Increased heart rate
Increased respiratory rate
Increased temperature
Sweating The causes of colic are not absolute and may include, but are not limited to:

Obstruction of the gastrointestinal tract from food or other materials
Impaction of food material in the gastrointestinal tract
Buildup of gas inside of the abdomen
Parasitic infestation by roundworms, tapeworms, cyathostomes, and/or strongyles
Dorsal displacement
Torsion of the gastrointestinal tract
Intussusceptions
Epiploic foramen entrapment
Strangulating lipoma
Mesenteric rent entrapment
Gastric ulceration
Enteritis
Colitis While many animals can suffer from colic, horses—especially those that are stabled—are particularly susceptible due to a multitude of factors, including heavily grain-based diets, relatively small stomach volume, the inability to release excess gas by eructation, susceptibility to parasitic infestation, and a highly convoluted gastrointestinal tract. Treatment for equine colic varies depending on the cause and severity of the condition ranging from rest and medication to invasive emergency surgery. Different types of colic include, but are not limited to:

Stomach distention: The small capacity of a horse's stomach makes it susceptible to distension when excessive amounts of food are ingested. When a horse gorges itself on grain, or a substance which expands when dampened like dried beet pulp, the contents of the stomach can swell. Unlike humans, horses have a valve at the distal end of their esophagus into the stomach that only opens only one way, and as a result horses cannot regurgitate. If something is eaten to disrupt their digestives system there is only one direction digesta can travel. The horse's small stomach and their inability to regurgitate may result in distension and potential rupture of the stomach.

Displacement: The small intestine is suspended in the abdominal cavity by the mesentery and is free floating in the gut. In a displacement, a portion of the intestine has moved to an abnormal position in the abdomen. This mobility can predispose the small intestine to become twisted. Except in rare cases, the result is total blockage of the intestine requiring immediate surgery. During twisted intestine surgery, the intestine is repositioned and any portion of the intestine that is damaged due to restricted blood flow is removed. Displacement colic can be caused by gas build up in the gut that makes the intestines buoyant and subject to movement within the abdominal cavity.

Impaction colic: Impaction colic occurs when the intestine becomes blocked by a food mass that's too large to easily pass. The large intestine folds upon itself and has several changes of direction (flexures) and diameter changes. These flexures and diameter shifts can be sites for impactions, where a firm mass of feed or other foreign material blocks the intestine. Impactions can be induced by coarse feed stuff, dehydration, or accumulation of foreign material.

Gas colic: Most cases of colic are associated with some gas build up. Gas can accumulate in the stomach as well as the intestines. As gas builds up, the gut distends, causing abdominal pain. Excessive gas can be produced by bacteria in the gut after ingestion of large amounts of grain or moldy feeds. The symptoms of gas colic are usually highly painful but non-life threatening unless untreated, and then displacement becomes a possibility.

Spasmodic colic: This occurs due to increased contractions of the smooth muscle in the intestines. These intestinal contractions, or abnormal spasms, cause the intestines to contract painfully. Over-excitement or over-stress of the animal can trigger spasmodic colic.

Sand colic: When fed on the ground in sandy regions sand can accumulate in the horse's cecum. The irritation can cause discomfort, and if there are significant amounts of sand present, the weight can cause the cecum to become displaced.

Enteritis/colitis: In some cases, abdominal pain is due to inflammation of the small intestine (enteritis) or large intestine (colitis). These conditions are the result of inflammation of the intestine, and may be caused by bacteria, grain overload, or tainted feed. Horses with enteritis/colitis may also have diarrhea. Enteritis and colitis are often hard to diagnose and may present themselves similar to displacement or impaction colic.

Parasite infections: Certain types of parasitic infections can cause colic. Strongyles, a type of parasitic worm, cause intestinal damage that can restrict blood flow to the intestine. Damage to the walls of the intestine produce a roughened surface that can accumulate clots. Other colic producing parasites in horses include ascarids (roundworms) and bot flies which can cause stomach blockage resulting in colic.

Stress: Travel, herd changes, schedule disruptions, and other traumatic events can contribute to stress in an animal which may result in colic.

Casting

Stall casting occurs when a horse lies down or rolls in a stall and gets trapped too closely to the wall. When this occurs the horse is not able to gain sufficient leverage and stand up. Subsequently, the horse may become frightened and begin thrashing, likely resulting in injury. Exhaustion to the point of shock is another concern with a distressed horse that is cast.

Nearly all cases of casting require human intervention to assist the animal to turn over. If the horse is relatively quiet, 2 persons may be able to reposition the horse by pulling it over gently by the tail or hind legs (with the aid of a lunge line), while simultaneously pulling the horse's head over. If the horse is too panicked, sedation may be required before any attempt is made to reposition and turn over the horse.

Foaling

Giving birth to a foal occurs over 3 stages. The ability for a caretaker to recognize each of these stages is critical to assess whether intervention is needed. However, the ability to have live human monitoring and evaluation 24 hours a day during the last few weeks of a 340-day gestation period is challenging for many.

Stage 1: Positioning of the Foal

During this stage (1-4 hours) the fetus gradually shifts from a position on its back and rotates until its heads and forelimbs are extended in the birth canal. Over several hours the pregnant mare may appear restless and become very nervous. She will likely have several transient periods of pacing, walking the fence line, and colic-like symptoms (e.g., pawing, kicking, rising/falling+/−healthy shake, rolling+/−thrashing). Mares in the pasture will also move away from other horses and towards complete isolation.

Stage 2: Delivery of the Foal

During this stage (15-20 minutes) the fetus moves down the birth canal, the mare's water breaks, and the foal is born. Due to very strong contractions of the abdominal and uterine wall muscles, the mare usually lies on her side (i.e., on her flanks) with her legs fully extended although she may also rise/fall several times to reposition the foal, sometimes with the foal's head and limbs protruding. During this stage it's important for the caretaker to check the position of the foal within the vagina; lower the foal to the ground if the mare is standing; reposition the mare away from any wall, fence, or other obstacle; and break open the amniotic sack and untangle the umbilical cord, if required.

Stage 3: Expulsion of the Placenta

During this final stage (1-8 hours), the placenta is expulsed. If the placenta has not been expulsed after 3 hours, the caretaker should alert a veterinarian. It is also important for the caretaker to tie-up the afterbirth in a knot such that it hangs over the mare's hocks during this period.

Problems with Current Technology

Although there are a few technologies (i.e., equine foaling/birthing monitors) on the market today, all these products have serious shortcomings. Their cumbersome design, rudimentary analytical methods, and limitations in wireless transmissions prevent them from being used reliability on a large scale as foaling/birthing monitors, let alone secondary use to assist in detecting colic, casting, or other distress states of animals.

Belly Bands: In practice, horses tend to become preoccupied with nipping at belly bands, making it a distraction for horses and staff. The belly band also introduces a new injury risk due to the transmitter unit mounted on the horse's back. A horse experiencing severe colic is likely to roll frequently and often. As such, a horse wearing the unit on its back is likely to roll onto the unit, which may result in a back injury. The methods for mounting this, which is similar to other foaling sensors on the market today, and the positioning of these sensors on a horse make them suboptimal for the detection of colic.

Behavior Analysis: Most foaling/birthing monitors rely solely on motion sensors to assess whether an animal is lying down or on its side for a specific period of time, which is likely to be plagued with many false-positive findings.

Radio Frequency Transmission: A few systems use simple radio frequency (RF) transmitters to signal an alarm when triggered. These systems can be connected to a phone line or pager to automatically alert caretakers. These systems use single-channel RF modulation to transmit sensor data. Because multiple transmitters interfere with each other and their surroundings (e.g., metal barns), the RF approach cannot be scaled-up for large operations with many horses or be used while in transit. Interference can also arise from other RF transmitters, such as cordless phones or other similar devices located nearby.

Given the deficiencies of the technologies cited above, barn managers resort to (if anything) round-the-clock night checks by caretakers and/or night watchmen to monitor the health and safety of their horses. Such laborious checks by humans are time consuming, subjective, costly, and not without error. Even with individuals on location twenty-four hours a day in a veterinary facility or barn, signs of distress or trouble might not be caught as early as desired. Accordingly, improvements are sought in the detection of animal distress and notification of caregivers. The present invention remedies many of these problems and limitations.

SUMMARY OF THE INVENTION

While the way that the present invention addresses the disadvantages of the prior art will be discussed in greater detail below, in general, the present invention provides a mobile adaptive sensor and notification system ("MASNS") for surveillance of animals, and more particularly for the analysis of biometrics (e.g., vital signs), biologic functions (e.g., digestion), and behaviors (e.g., posture, motion patterns) that may indicate a variety of problematic health conditions, some of which may result in serious injury or death of the animal. The vital signs of an animal, coupled with its biologic functions, posture, and actions/movements can directly correlate with a physiological state and behaviors that are indicative of distress (e.g., colic), trauma (e.g., casting), other conditions where human intervention is warranted (e.g., foaling).

There are over 9.2 million horses estimated to be in the United States (>58 million worldwide), with more than 40% of these animals being kept for recreational purposes, nearly another 40% being kept for performance competitions (i.e., racing and showing), and the balance being kept for farm, ranch, and police work, as well as use in rodeos, polo matches, and as carriage horses. When a horse is transported or used heavily for performance competitions their stress levels increase and subsequently their chance for developing colic or becoming cast tends to be more frequent. Colic and casting are especially serious issues with high-value horses, which are more likely to be transported for performance competitions and breeding.

When a horse is experiencing colic and/or is cast, the animal will be in a distressed state as evidenced by measurable changes in biometrics (e.g., vital signs) and biologic functions (e.g., digestion), posture (e.g., lying down), and repeated characteristic motion patterns (e.g., pawing, kicking, rising/falling+/−healthy shake, rolling+/−thrashing). When this occurs, human intervention is needed to assess the severity of distress and establish a care plan. Mild cases of colic may be resolved by simply hand-walking a horse for 15 minutes, whereas severe cases of colic may require invasive emergency surgery. A cast horse may sometimes reposition themselves to stand-up independently, but more often human intervention is needed to assist the animal. A mare who is about to foal will also have measurable changes in her vital signs and a well-characterized set of recurrent actions and movements. Identification of these changes in biometrics and behaviors will signal the start of stage 1, and therefore an important time for the caretaker to be present to monitor and address any complications that may arise. Regardless of whether a horse is experiencing colic, is cast, or is having foaling complications their outcome is directly correlated with time to intervention. Delay of intervention is a negative prognostic indicator that has dire impact on outcomes, including permanent injury and even death.

Early detection of animal distress, such as colic in horses, may lead to prompt treatment that can vastly improve outcomes and increase the animal's chances of survival. Due to the high cost of colic surgery and poor survival outcomes with untreated colic, it is especially desirable for the animal to receive medical treatment at the first signs of colic. Thus, a reliable mobile animal surveillance and distress monitoring system in the form of a wearable MASNS noninvasively attached to an animal that can relay a notification to caretakers—when signs of distress and other serious conditions that require immediate intervention are identified—is useful in safeguarding horses without the need for humans to be present for round-the-clock monitoring.

The MASNS and method of its use disclosed herein comprises a multiplex set of sensors for measuring biometrics, monitoring biologic functions, evaluating posture and motion patterns, assessing environmental factors, and determining the exact location of an animal; a computational processor for real-time analysis of all sensor inputs to identify, differentiate, and validate specific states and behaviors of an animal; and a wireless transceiver for bidirectional communications to transmit notifications to a caretaker, receive user queries, and update the system's software and firmware. The system can be configured to monitor the physiological state, biologic functions, behavioral patterns, and location of a wide variety of animals including, but not limited to, horses, cattle, elk, llamas, bison, bears, sheep, deer, companion animals (i.e., dogs, cats), etc.

One application for the MASNS is the broad surveillance of horses to detect novel events. Novel events are described as those biometrics, biologic functions, and/or behavioral activity that are outside the defined parameters and limits of the system. Another application is the continuous monitoring of horses where biometrics, biologic functions, and/or behavioral activity is analyzed within the predefined parameters and predefined limits of the system. The system detects changes in biometrics and biologic functions compared with both defined parameters and limits (for training of the model) and adaptively-derived thereafter to each animal's unique historical and empirical values/thresholds. The system also evaluates posture and actions/movements compared to each animal's historical "normal" behavior and characteristic motion patterns that may be indicative of colic, casting, foaling, or other serious conditions that require immediate intervention. Various MASNS embodiments may contain any combination of an ultrawide band-impulse radar ("UWB-IR"), a thermal infrared sensor ("TIRS"), a microphone, a 3-axis accelerometer, a 3-axis gyroscope, a 3-axis magnetometer, a single-axis barometric pressure sensor, an optical light sensor, and a location sensor (e.g., GPS, Wi-Fi or cellular triangulation).

The UWB-IR, TIRS, and microphone outputs correlate with the general physiologic state of the animal, and are used as a first-level filter to identify a possible distress state. The accelerometer, gyroscope, magnetometer, barometric pressure sensor, and location sensor outputs correlate with coarse posture, position, and motion information, and are used to classify behavior as "normal" vs. "non-normal" as well as qualify the type of actions and motions (e.g., pawing, kicking, rising/falling+/−healthy shake, rolling+/−thrashing). Finally, the optical light sensor correlates with the environmental conditions of the animal (e.g., inside/artificial light vs. outside/natural light).

The MASNS analyzes all biometric, biologic function, behavioral, and environmental inputs, to determine the presence and relative degree of distress using a fuzzy logic-based model. In this model multiple inputs are evaluated to derive a single quantitative output measure of relative distress (i.e., an Equine Distress Index ["EDI"]), ultimately informing the system whether or not to issue one or more wireless multi-level notifications (e.g., "watch" vs. "warning" vs. "alert"). If the sensor unit detects biometrics and/or biologic functions outside acceptable limits for an unusual period of time along with characteristic postures and/or motion patterns that are outside normal limits for an unusual period of time, algorithms compare the data with predefined parameters and historical value/thresholds for each individual animal to determine if a distress situation is occurring and to remotely/wirelessly trigger a notification via a communication protocol. When notification is triggered or when the system is queried, the outputs of the GPS unit and/or triangulation via Wi-Fi or cellular signal strength correlate with the latitudinal and longitudinal coordinates of the animal wearing the MASNS device and can be used to precisely locate the distressed animal.

The device may be implemented to continuously monitor horses in a variety of locations including, but not limited to, stalls, pastures, breeding centers, show barns, and veterinary clinics, as well as in trailers, trucks, vans, and/or other modes of transportation. When distress is detected, the device may relay the emergency situation to appropriate caretakers via wireless communication methods in a cascading or escalating fashion.

Various research applications are also enabled by the monitoring, such as identifying more subtle conditions based on biometrics, biologic functions, and behavioral signatures of wild horse herds. Macro analysis of historical data for larger aggregate populations and smaller cohorts may also lead to the discovery of new risk factors and/or markers of early onset colic and/or other conditions. The opportunity to perform predictive analytics on the system's data may also prove beneficial to policy makers, insurance providers, and others interested in protecting the welfare or horses and their owners.

One aspect of the invention features, in some embodiments/applications, a method for remote animal surveillance and distress monitoring. The method includes detecting one or more biometric parameter of the animal; detecting one or more behavioral parameter of the animal; determining occurrence of a novel event based on comparison of detected parameters to a range of predefined parameter values and qualifications; computing a composite value for a combination of detected parameters; determining whether the composite value exceeds a predefined composite threshold value indicative of possible distress in the animal; and notifying one or more remote caretakers of possible distress in the animal based on the composite value exceeding the predefined composite threshold value.

In some embodiments/applications, determining occurrence of a novel event includes determining when one or more of the detected parameters fall outside one or more of predefined parameters or historical parameters for the animal.

In some embodiments/applications, determining occurrence of a novel event comprises use of a one-class classifier.

In some embodiments/applications, the method includes detecting one or more biologic function parameter of the animal and using detected biologic function parameters for at least one of determining the occurrence of a novel event and computing the composite value.

In some embodiments/applications, the method includes updating the range of predefined parameter values and qualifications, and composite threshold values in an ongoing fashion to conform to detected parameters for the animal over time.

In some embodiments/applications, the method includes use of fuzzy logic to derive the composite value.

In some embodiments/applications, notifying one or more caretakers includes activation of an escalating notification protocol across multiple channels.

In some embodiments/applications, the one or more biometric parameter includes one or more of a respiratory rate, heart rate, and temperature of the animal.

In some embodiments/applications, detecting the one or more behavioral parameters includes monitoring data from one or more of an accelerometer, gyroscope, magnetometer, and barometric pressure sensor.

Another aspect of the invention features, in some embodiments/applications, a method for detecting one or more biometric parameter in animals. The method includes using UWB-IR to acquire one or more of respiratory rhythm data and cardiac rhythm data; differentiating between the respiratory rhythm data and the cardiac rhythm data by filtering and principal component analysis followed by independent component analysis for feature reduction and extraction through conditioning of acquired rhythm data; using fast Fourier transform for frequency analysis of the conditioned rhythm data to determine a power level of respective dominant frequencies; and correlating the respective dominant frequencies with a respiratory signal and a cardiac signal of the animal.

In some embodiments/applications, the method includes determining when one or more of a respiratory rate and a cardiac rate of the animal exceeds one or more of a predefined threshold or historical threshold indicative of possible distress in the animal.

In some embodiments/applications, the method includes notifying one or more remote caretakers of the possible distress in the animal based on the determining.

Another aspect of the invention features, in some embodiments/applications, a method for mobile equine surveillance and distress monitoring. The method includes monitoring at least one of the respiratory rate and the heart rate of an animal using UWB-IR; monitoring the temperature of an animal using a thermal infrared sensor; monitoring the behavior of the animal using at least one of an accelerometer, gyroscope, magnetometer, and barometric pressure sensor; determining the posture and location of the animal using at least one of a barometric pressure sensor, global positioning system sensor, and Wi-Fi triangulation; determining when at least one parameter of the respiratory rate, heart rate, temperature, behavior, and posture of the animal meets a single threshold value; determining when a combination of parameters of the respiratory rate, heart rate, temperature, behavior, and posture of the animal meets a composite threshold value indicative of possible distress in the animal; and activating of an escalating notification protocol across multiple channels to inform one or more remote caretakers of possible distress in the animal.

In some embodiments/applications, the method includes detecting one or more biologic function parameter of the animal.

In some embodiments/applications, the method includes monitoring of digestive activity of the animal using a microphone.

In some embodiments/applications, the method includes detection of one or more novel events though use of a one-class classifier when one or more detected biologic function parameter falls outside one or more of predefined parameters or historical parameters for the animal; and updating a range of predefined biologic function parameter values and qualifications, single threshold values, and composite threshold values in an on-going fashion to conform to detected parameters for the animal over time.

In some embodiments/applications, the method includes determining occurrence of one or more novel events though use of a one-class classifier when one or more detected parameters fall outside one or more predefined parameters and historical parameters for the animal;

In some embodiments/applications, the method includes updating a range of predefined parameter values and qualifications, single threshold values, and composite threshold values in an on-going fashion to conform to detected parameters for the animal over time.

In some embodiments/applications, the method includes sending a notification when one or more of the heart rate, respiratory rate, and temperature is outside an adaptively-derived empirical upper limit of normal and lower limit of normal for the animal while at rest.

In some embodiments/applications, the method includes generating one or more of a first watch notification when the heart rate is greater than about 15% above the resting normal (RN) or is greater than about 15% below the RN for a period of time, a second warning notification when the heart rate is greater than about 40% above the RN or is greater than about 40% below RN for a period of time, and a third alert notification when the heart rate is greater than about 70% above the RN or is greater than about 70% below RN for a period of time. The method further includes generating one or more of the first watch notification when the respiratory rate is greater than about 35% above the RN or is greater than about 35% below RN for a period of time, the second warning notification when the respiratory rate is greater than about 75% above the RN or is greater than about 50% below the RN for a period of time, and the third alert notification when the respiratory rate is greater than about 150% above the RN or is greater than about 65% below the RN for a period of time. The method further includes generating one or more of the first watch notification when the temperature is greater than about 1% above the RN or is greater than about 1% below the RN for a period of time, the second warning notification when the temperature is greater than about 2% above the RN or is greater than about 1.75% below the RN for a period of time, and the third alert notification when the temperature is greater than about 4% above the RN or is greater than about 3.5% below the RN for a period of time.

BRIEF DESCRIPTION OF THE DRAWINGS

A more complete understanding of the present invention may be derived by referring to the detailed description and claims when considered in connection with the Figures, wherein like reference numerals refer to similar elements throughout the Figures. Understand that Figures depict only certain embodiments of the invention and are therefore not to be considered limiting of its scope. Embodiments will be described and explained with additional specificity and detail through the use of the accompanying Figures.

FIG. 4A illustrates one embodiment of a MASNS decision matrix: Watch notification.

FIG. 4B illustrates one embodiment of a MASNS decision matrix: Warning notification.

FIG. 4C illustrates one embodiment of a MASNS decision matrix: Alert notification.

FIG. 16B illustrates one embodiment of a behavior classifier for a specific target behavior.

DETAILED DESCRIPTION OF SELECTED EMBODIMENTS

Figure 1:
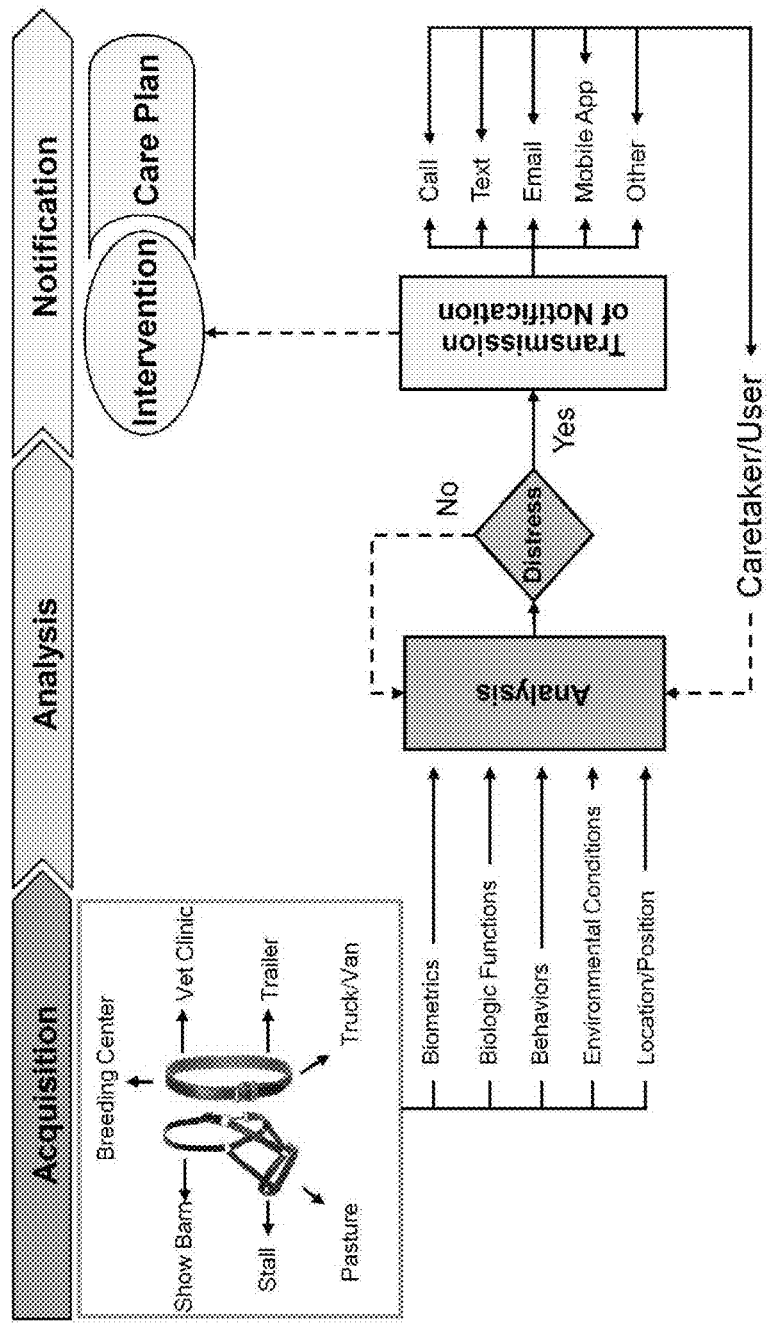
FIG. 1 illustrates one embodiment of Mobile Animal Surveillance and Distress Monitoring.

The following description is of exemplary embodiments of the invention only, and is not intended to limit the scope, applicability or configuration of the invention. Rather, the following description is intended to provide a convenient illustration for implementing various embodiments of the invention. As will become apparent, various changes may be made in the function and arrangement of the elements described in these embodiments without departing from the scope of the invention as set forth herein. It should be appreciated that the description herein may be adapted to be employed with alternatively configured devices having different shapes, components, sensors, mechanisms and the like and still fall within the scope of the present invention. Thus, the detailed description herein is presented for purposes of illustration only and not of limitation.

Reference in the specification to "one embodiment" or "an embodiment" is intended to indicate that a particular feature, structure, or characteristic described in connection with the embodiment is included in at least an embodiment of the invention. The appearances of the phrase "in one embodiment" or "an embodiment" in various places in the specification are not necessarily all referring to the same embodiment.

In the following description, numerous specific details are provided for a thorough understanding of specific embodiments. However, those skilled in the art will recognize that embodiments can be practiced without one or more of the specific details, or with other methods, components, materials, etc. In some cases, well-known structures, materials, or operations are not shown or described in detail in order to avoid obscuring aspects of the embodiments. Furthermore, the described features, structures, or characteristics maybe combined in any suitable manner in a variety of alternative embodiments. Thus, the following more detailed description of the embodiments of the present invention, as represented in the drawings, is not intended to limit the scope of the invention, but is merely representative of the various embodiments of the invention.

Disclosed are embodiments of mobile animal surveillance and distress monitoring systems, in the form of a wearable MASNS that analyzes real-time biometrics, biologic functions, behaviors, and environmental conditions associated with the health and safety of animals, as well as coordinates to track location of animals. The MASNS includes a multiplex of sensors, a power source, a processing unit, a wireless transceiver, data analysis functions, one-class classifiers, algorithms, bi-directional communication protocols, and a means for associating the system with an animal for long-term mobile surveillance (e.g., wearable smart technology apparatus in the form of a harness and/or clothing). The embodiments described herein are presented within the context of equines, but it should be obvious to one skilled in the art the MASNS is applicable to a host of different animals under a myriad of conditions. Equine health issues, such as colic, casting, and foaling, are indicated by changes in a horse's biometrics, biologic functions, posture, and key characteristic motion patterns. The MASNS detects such indicative biometric changes, biologic functions, and behavioral patterns by monitoring the horse's physiologic state, posture, and actions/movements.

System Overview

With reference to FIG. 1, the method for remote animal surveillance and distress monitoring comprises 3 phases: acquisition, analysis, and notification. During the acquisition phase the MASNS device is continuously obtaining data on an animal at home, at a breeding center, at a show barn, at a vet clinic or other establishment regardless of whether in a stall or pasture, or while in transit on a trailer, truck, or van. During the analysis phase, the device determines the location, general state, and well-being of the animal by processing and evaluating real-time biometrics, biologic functions, behaviors, and environmental conditions at the point-of-care (i.e., at the level of the animal). If the system determines that the animal is experiencing distress during this analysis phase, the MASNS will proceed to the notification phase and send a wireless signal to a central computing station where a predefined cascading communication protocol will be executed to notify the animal's caretaker(s) of their distress state and location for intervention. At any point the caretaker(s) or other authorized user can remotely query the MASNS device and receive, via a visual dashboard from a computer, tablet, or smart phone, real-time and historical metrics on data acquired.

Physical Design

One or more MASNS devices are associated/affixed to an animal within small water-tight and dust-resistant enclosure(s) containing sensors and electronic components remotely mounted on an animal via a smart-technology apparatus (e.g., harness, clothes) to monitor its biometrics, biologic functions, behaviors, environmental conditions, and location around the clock or at designated intervals without the need for human supervision or effort.

With continued reference to FIG. 1, in one embodiment, the MASNS device is seamlessly integrated within a horse's safety/breakaway halter or collar. In different embodiments, the MASNS device can be non-invasively attached to a facial apparatus (e.g., halter, bridle), neck apparatus (e.g., collar, neck sweat), surcingle, sheet/blanket/hood, or other horse tack or equipment as appropriate. For other animals, the MASNS device can be attached to the animal using ear tags, harnesses, ankle bands, tail mounts, or other appropriate techniques. Further, in another embodiment, the MASNS device (whole are in part) may be associated with the animal in vivo.

In one embodiment, the sensor's enclosure(s) bend to follow the natural contour of the horse's head, poll, and neck. In other embodiments the sensor's components fit in a single small enclosure. The small, integrated, water-tight and dust-resistant features of the MASNS device makes it suitable for routine long-term use in a wide range of business settings and operations. In one embodiment, because the MASNS device is integrated and contained within a horse's safety/breakaway halter or collar, the device poses little risk of snagging on fences, feeders, or other objects, nor does it protrude or have an unusual appearance that may attract the curiosity of other horses.

Figure 2:
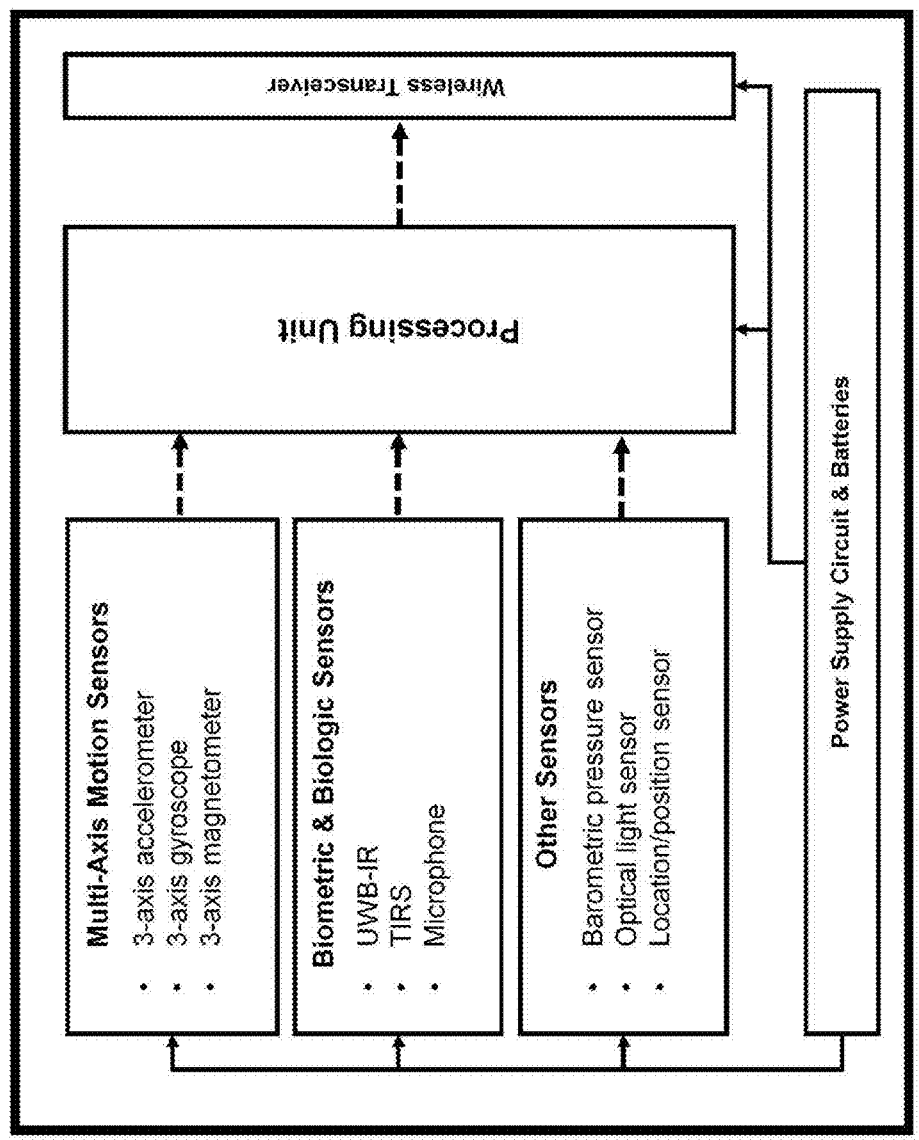
FIG. 2 illustrates one embodiment of a MASNS module.

With reference to FIG. 2, one embodiment of the MASNS remote unit includes, but is not limited to multi-axis motion sensor(s), biometric sensor(s), biologic sensor(s), single-axis barometric pressure sensor(s), optical light sensor(s), location/position sensor(s), electronic module(s) with microcontroller(s) and microprocessor(s), battery(s), wireless transceiver(s), and other associated electronics/additional components. The individual components can be arranged in the remote unit enclosure(s) in a variety of configurations. The microprocessor is programmed to analyze and control the functions of the electronic components in the MASNS device. The multi-axis motion sensor(s), barometric pressure sensor(s), and location/position sensors can provide coarse posture and location information (e.g., the sensors' tilt angle in multiple dimensions), as well as fine motion information (e.g., pacing, shaking, struggling). The transceiver is the basis for receiving a signal from a user device, as well as for wireless communication of the distress indicator alarm once activated.

The remote unit's noninvasive design, long battery life, and wireless communication capabilities makes it a safe, convenient, and practical solution for routine, long-term monitoring of animal health and safety and is suitable for adoption in large-scale operations such as breeding centers, show and racing barns, and veterinary clinics and hospitals.

MASNS Decision-Making Protocol

Figure 3:
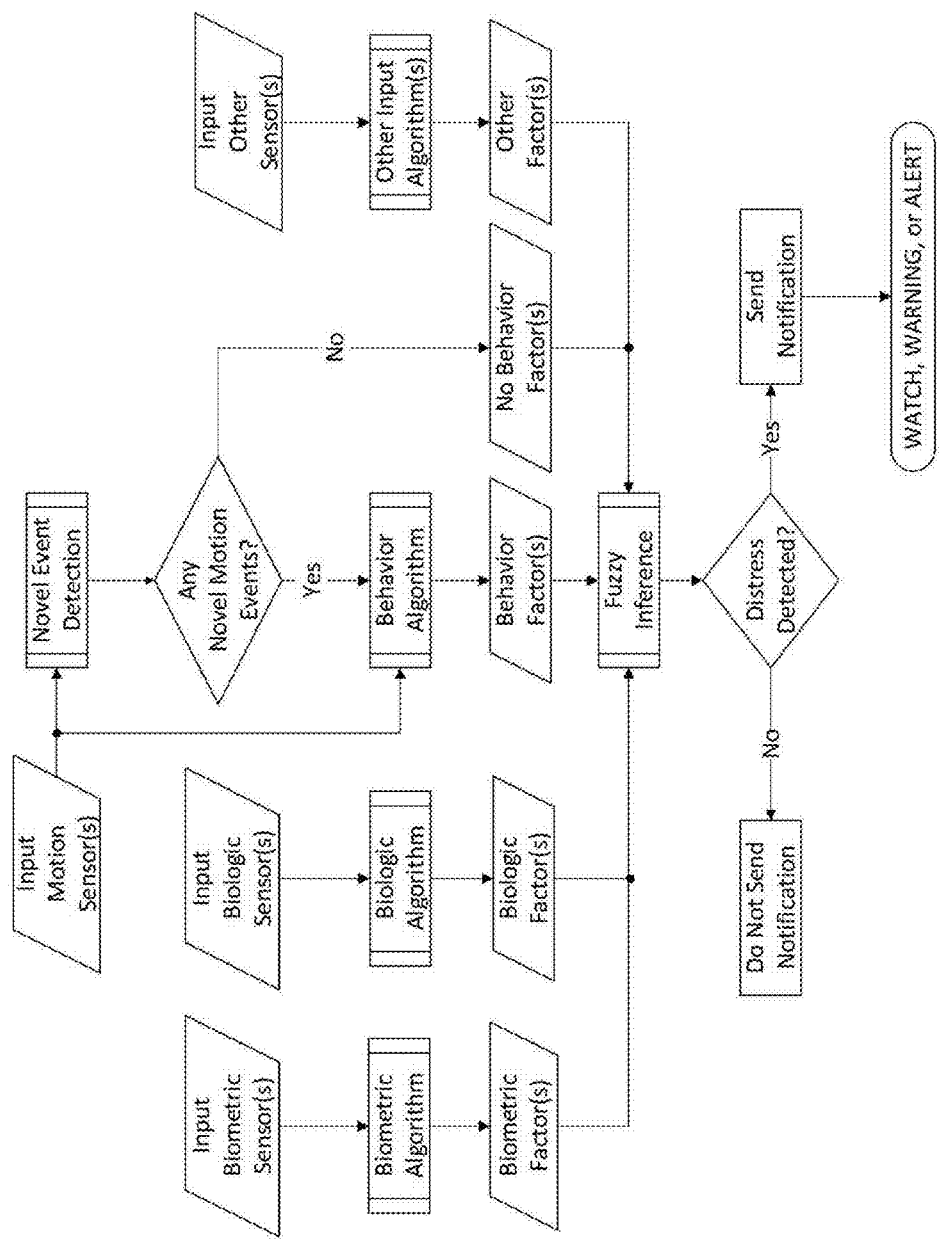
FIG. 3 illustrates one embodiment of a MASNS decision-making protocol.

In order for the MASNS device to determine whether or not to send a notification indicating the animal is in distress, a systematic protocol is followed. With reference to FIG. 3, one embodiment of the MASNS decision-making protocol includes three parallel detection paths with their respective sensor suites (i.e., biometric sensors, biologic sensors, motion sensors) and one additional path for inputs from other sensors (e.g., barometric pressure sensors, location/position sensors, optical light sensors). Each sensor suite feed respective detection algorithms (i.e., biometric algorithm, biologic algorithm, behavior algorithm, and novel-event detection ["NED"] algorithm). Biometric information can include, e.g., heart rate, respiratory rate, body temperature, etc. Biologic information can include, e.g., digestive/gut sounds, groaning sounds, bowel movements, abdominal distension, perspiration, etc. Behavioral information can include, e.g., rise, fall, roll, lie down, shake, flank watch, paw, kick, spin, flehmen response, bruxism, windsuck, crib, weave, etc. as well as new and novel actions and movements considered unique when compared to that animal's historical behavior.

The NED algorithm determines whether or not the equine is in a "normal" or "novel event" state based on motion sensor(s) and its trained classifier. If a novel event is not detected, the animal is behaving normal and the MASNS does not need to generate a notification. If a novel event is detected, then the window of the novel event is sent to behavior algorithm for further evaluation. The behavior algorithm determines whether the novel event is one of the target behaviors known to serve as a surrogate marker of distress or other state that may require human intervention. If the novel event is not one of the target behaviors, the MASNS does not need to generate a notification. If the novel event is one of the target behaviors, then the behavior algorithm sends the target behavior and its parameters to a fuzzy inference system (FIS) for an overall quantitative measure of relative distress or EDI.

Similarly to the behavior algorithm, the biometric and biologic algorithms detect and prepare the biometric and biologic data of the same time interval. If any of the biometric or biologic algorithm output values are within normal ranges, the MASNS does not generate a notification. If any of the biometric or biologic data are out of normal ranges, then they are sent to the FIS for further evaluation and an overall quantitative measure of relative distress or EDI.

Figure 5:
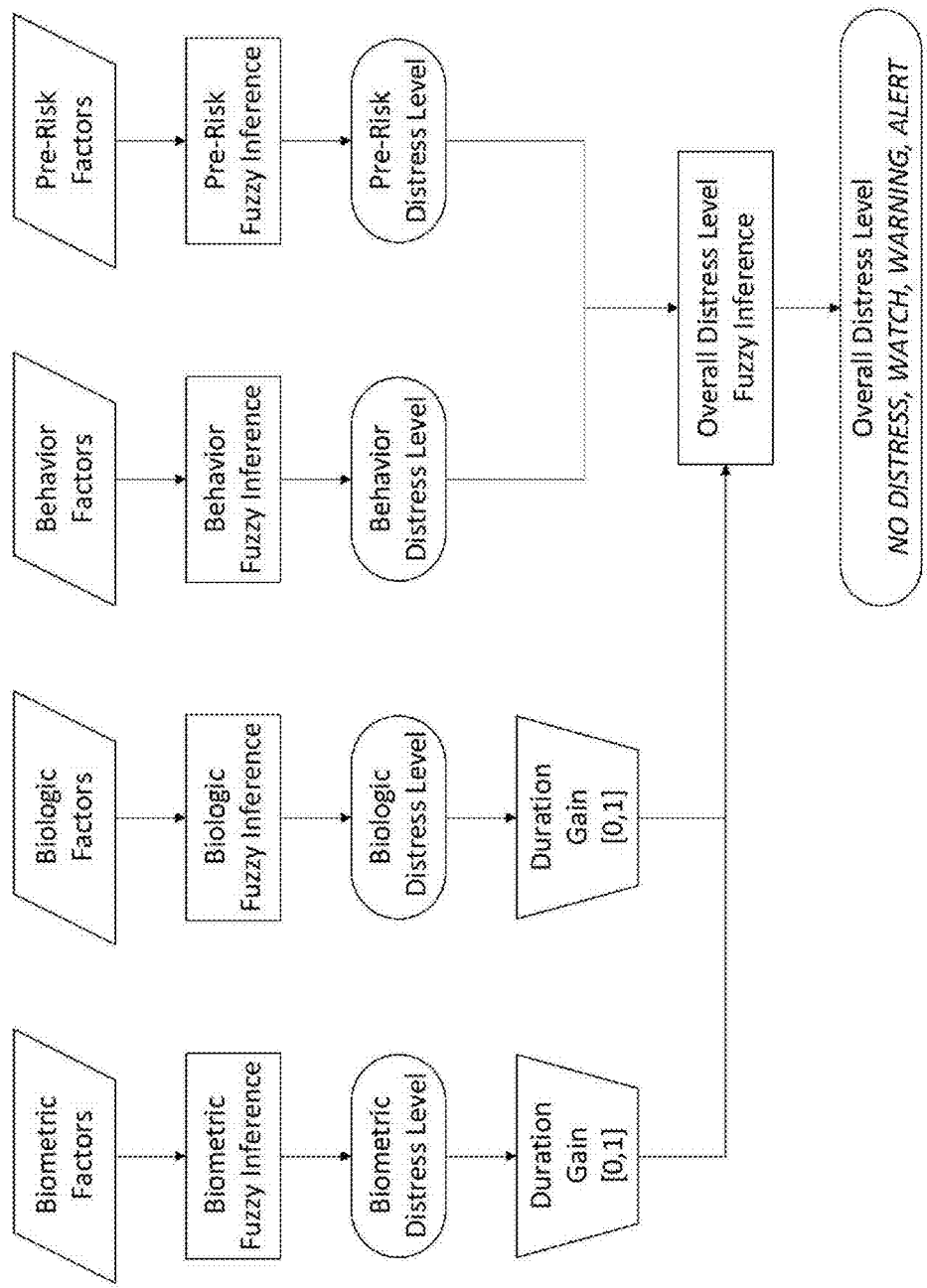
FIG. 5 illustrates one embodiment of a hierarchy of FISs for overall distress.
Figure 6:
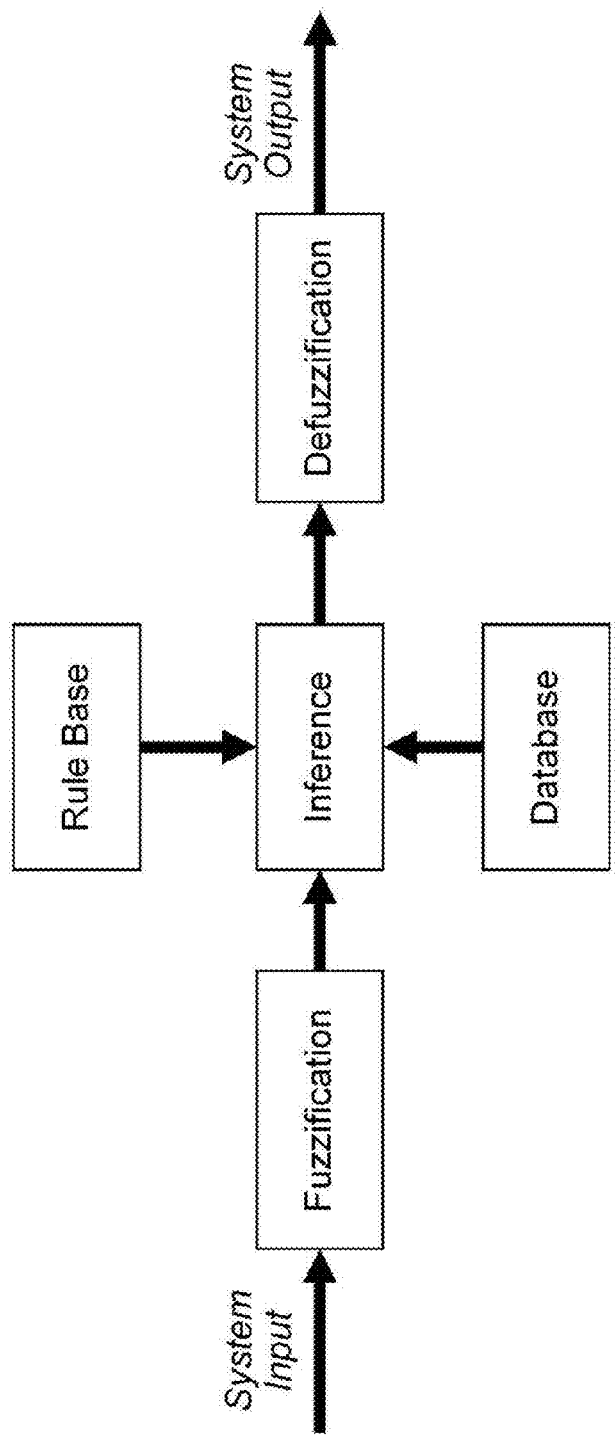
FIG. 6 illustrates an example of membership functions within a fuzzy system.

With reference to FIGS. 4A-C, in some embodiments, the MASNS decision-making protocol uses decision matrix criteria as the basis for creating the fuzzy rule base and shape of fuzzy membership functions of the FIS as shown in FIG. 5 and FIG. 6. The outputs of the biometric algorithm, biologic algorithm, behavior algorithm, and inputs from other sensors all feed into the FIS. In the FIS, data from algorithms and inputs from other sensors are evaluated and a multi-level notification in the form of "Watch," "Warning," or "Alert" is generated.

Fuzzy Logic

Fuzzy systems make use of input variables that are represented as fuzzy sets as opposed to crisp values. These fuzzy sets are used to attempt to quantify some uncertainty, imprecision, ambiguity, or vagueness that may be associated with a variable. Commonly, these fuzzy systems are defined by using if-then rules. A FIS is an application of fuzzy logic that can be utilized to help online decisions processes. A rule-based fuzzy system is typically realized as a set of sub-systems including a Fuzzifier, Fuzzy Database, Fuzzy Rule Base, Fuzzy Inference, and a Defuzzifier as shown in FIG. 6.

Fuzzification

Fuzzification is defined as the mapping of a crisp value to a fuzzy set. A fuzzifier represents the fuzziness of a variable by defining membership functions. There are three popular fuzzifiers that are used, singleton, Gaussian, and triangular. With a Gaussian or triangular fuzzifier some of the uncertainty with a system variable may be described and can help reduce noise. Singleton fuzzifiers generally do not provide this noise suppression.

Fuzzy Database

The database for a rule-based fuzzy system is the set of linguistic terms and their membership functions. Fuzzy membership functions are functions that define a mapping of an input set to its belonging to the fuzzy membership set itself (membership degree). A membership degree of '0' indicates the input set does not belong to the fuzzy membership set, whereas a '1' indicates full membership. There are many different fuzzy membership functions that can be used such as triangular, trapezoidal, Gaussian, bell, sigmoidal, and many others. For each membership function defined for an input space, a linguistic term is assigned to it; such as HIGH, LOW, AVERAGE, NEGATIVE, POSITIVE, etc.

For an example of a database for a FIS, consider a temperature sensor. Three general membership functions could be linguistically defined COLD, WARM, and HOT. From the linguistic terms it is the designer's choice how these membership functions are to be shaped (possibly based on empirical evidence).

Fuzzy Rule Base

For rule-based fuzzy systems, variables and their corresponding relationships are modeled through the means of if-then rules. The general form of these if-then rules is:

IF antecedent proposition THEN consequent proposition

Using a linguistic fuzzy model, as introduced by Mamdani, the antecedent and consequent are fuzzy propositions. The general form of a linguistic fuzzy model if-then rule follows as:

Ri: If $\tilde{x}$ is Ai Then $\tilde{y}$ is Bi

Where $\tilde{x}$ is the input (antecedent) linguistic variable, and Ai are the antecedent linguistic values of $\tilde{x}$. The output (consequent) linguistic variable is represented as ŷ with Bi corresponding to the consequent linguistic values of ŷ. The linguistic terms, Ai, are fuzzy sets that defines the fuzzy region in the antecedent space for respective consequent propositions. Ai and Bi are typically predefined sets with terms such as Large, Small, High, Low, etc. Using these linguistic terms an example of a linguistic fuzzy model if-then rule could be:

If temperature is HIGH Then risk is HIGH

Most systems are Multiple-Input and Single-Output (MISO) or Multiple-Input and Multiple-Output (MIMO). For MISO and MIMO systems the antecedent and consequent propositions can be a combination of univariate fuzzy propositions. The propositions may be combined using common logic operators such as conjunction or disjunction. The general rule form for a MISO system is below:

Ri: If x1 is Ai,1 and/or x2 is Ai,2 and ... xp is Aip Then y is Bi

Substituting in some linguistic terms, an example of a MISO rule would be:

If temperature is MED and breathing is HIGH Then risk is MED-HIGH

Fuzzy Inference

The inference procedure or compositional rule of inference is determined by two operators: implication operator and composition operator. The two most common compositional rules of inference are Mamdani and Larsen. Each of these have different operators to implement implication and composition.

Figure 7:
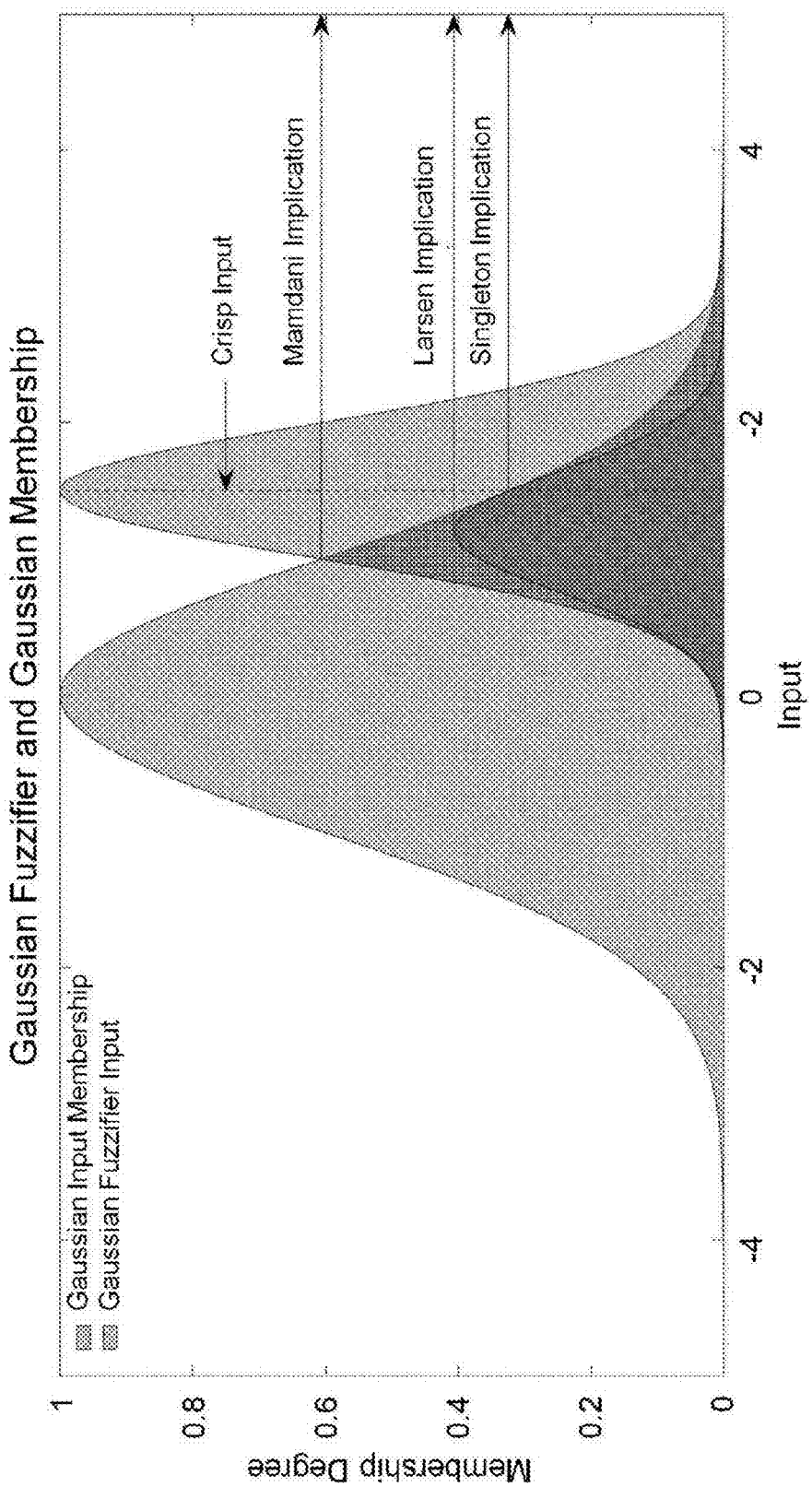
FIG. 7 illustrates an example of Mamdani and Larsen composition and implication operators.

Mamdani
Implication: min operator
Composition: max-min
Larsen
Implication→algebraic product operator
Composition→max-product The difference in implementation of the different implications is shown in FIG. 7.

Defuzzifier

The output of the FIS is multiple fuzzy sets that correspond to the degree of influence each rule has on the output. In order to generate a crisp value for the inference, the rule sets need to be aggregated and then defuzzified. One of the most common defuzzification techniques are Center of Gravity (CoG) or centroid, and the weighted average. The CoG technique is most accurate but can be computationally expensive, where the weighted average can provided a good estimate with significantly less computation.

The overall assessment of distress is determined on the basis of many factors within the entire system, including biometric, biologic, behavioral, and preexisting risk factors. Biometric and biologic factors include input from processing algorithms that provide information such as heart rate, respiratory rate, temperature, and possibly digestive indicators. Behavioral factors provide information about daily behavior based on motion data by estimating behavioral repetition, duration, and time-based relationships. The preexisting risk factors involve qualitatively assessing predisposal to distress based on environmental conditions, physical characteristics, and preexisting health issues. In order to provide an overall quantitative measure of relative distress or EDI from all these factors a hierarchy of FIS is used. The overall hierarchy is seen in FIG. 5.

With reference to FIG. 5, it is seen that each FIS uses information from a subset of the factors to provide a level of distress for each of the respective subsets of factors. Then each subset's distress level is provided to final FIS for an overall quantitative measure of relative distress or EDI, and decide if any of three notification levels are warranted. These notification levels include "watch, warning," and "alert" each respectively relating to increasing levels of distress. An additional gain stage is used for the biometric and biological inference systems to adjust the level of distress based on duration. These duration adjustments are to reduce false distress assessments from biometric and biologic changes that may occur during elevation in normal physical activity or noise from sensor readings. The actual implementation of each FIS can be generically described through the provided case studies detailed below.

Example/Case Study Fuzzy Inference System

This section provides a case study of how the implementation of an individual FIS is achieved. For this case study, the biometric system inputs are used as they are best fit for fuzzy logic memberships and logistic terms. In this section, the use of fuzzifiers are explained, preliminary generation of membership functions/linguistic terms for the database are provided, an example rule base discussed, and a potential defuzzification method visualized.

Fuzzification of Biometric Input

Each of the biometric inputs provides a crisp value for their estimate of a biometric reading. For the biometric inputs to be used in a fuzzy inference system, the crisp biometric value requires fuzzification. As discussed in the introduction, the most common fuzzifiers are singleton, Gaussian and triangular. A non-singleton fuzzifier is chosen since the reported biometric inputs have some uncertainty associated with their estimates. More specifically, a Gaussian fuzzifier is used because of the ease of computation and implementation over a triangular fuzzifier. A Gaussian fuzzifier is shaped per biometric input such that the Gaussian fuzzifier's variance corresponds to the uncertainty of the biometric inputs.

Fuzzy Database: Membership Functions and Linguistic Terms

Figure 8:
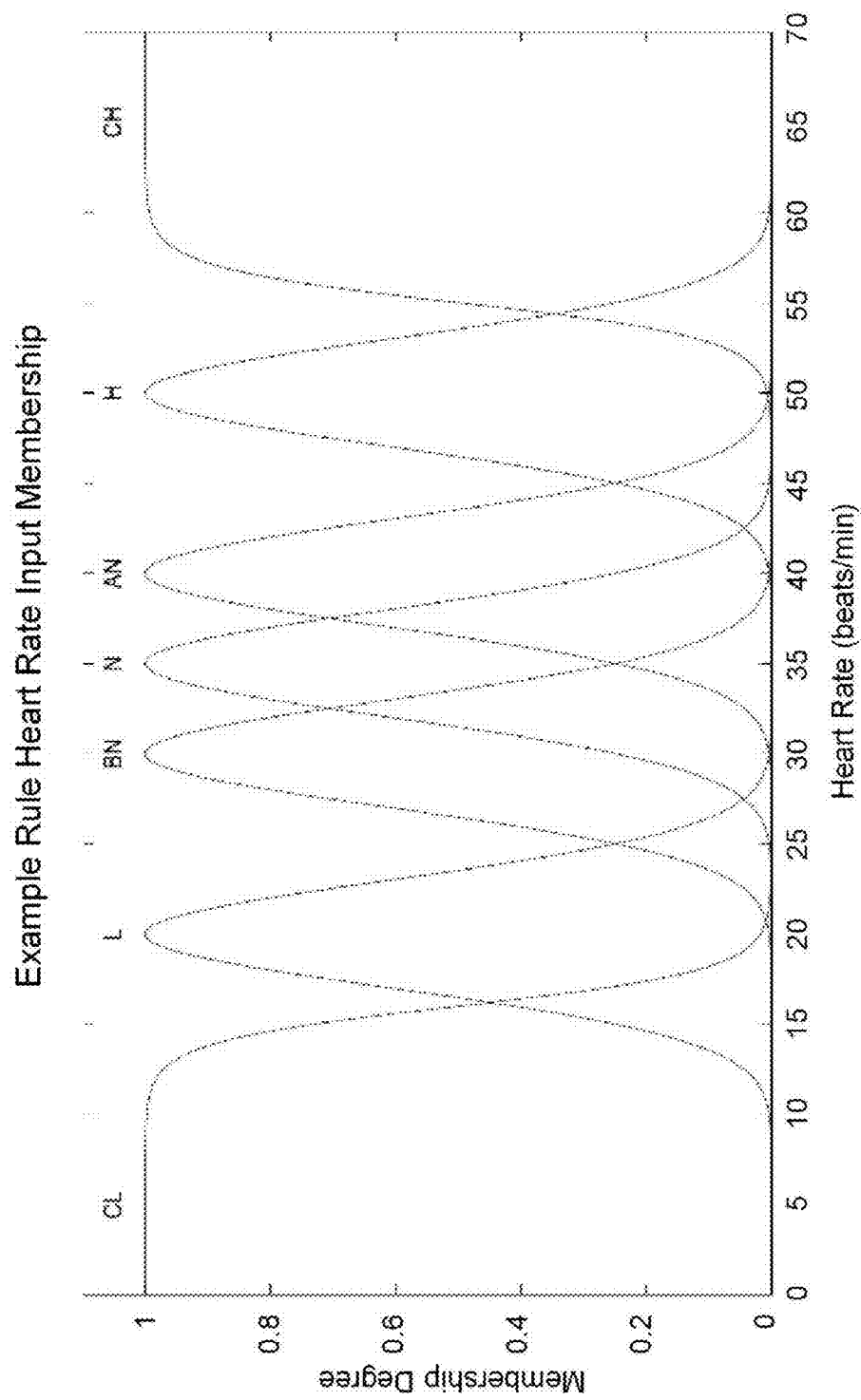
FIG. 8 is a graphical representation of input membership functions and shape for heart rate.
Figure 9:
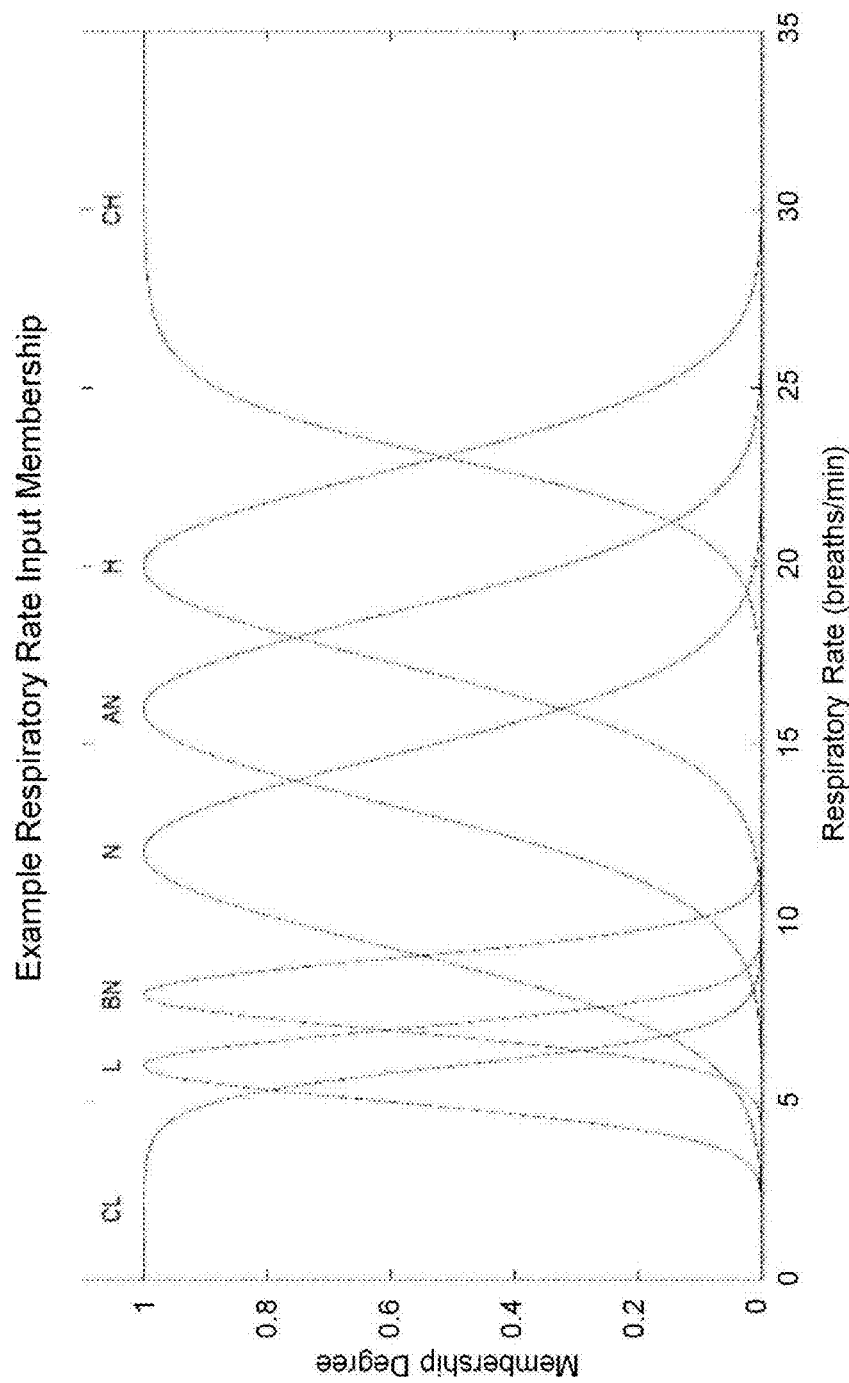
FIG. 9 is a graphical representation of input membership functions and shape for respiratory rate.
Figure 10:
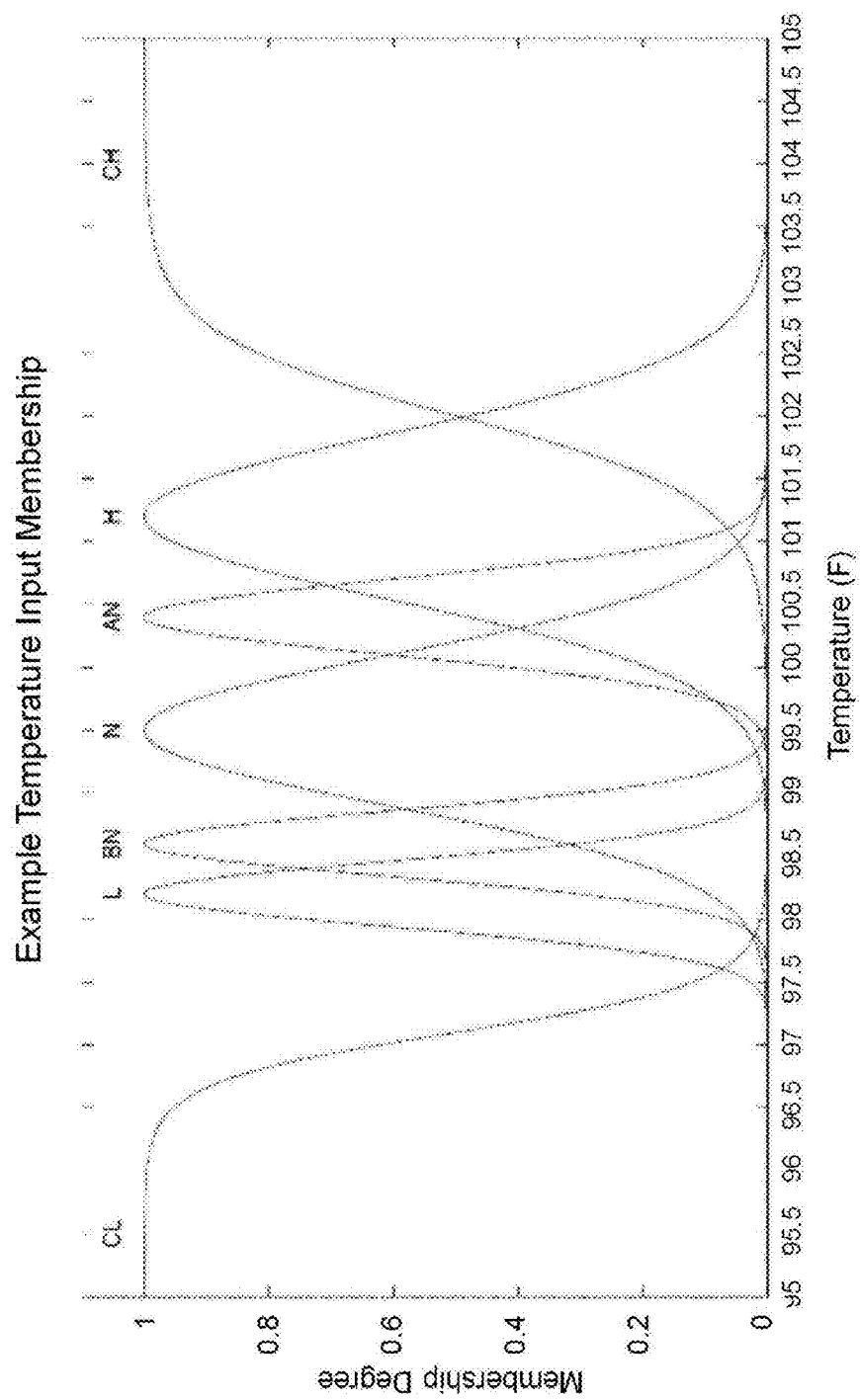
FIG. 10 is a graphical representation of input membership functions and shape for temperature.

The input membership functions are chosen to be Gaussian and sigmoidal for their potential reduction in computation in comparison to triangular/trapezoidal membership functions. The actual shape of these member functions are determined by a few parameters per membership. The parameters themselves are selected based on criteria provided by the decision matrix shown in FIGS. 4A-C. FIGS. 8-10 are example input memberships. Actual shapes of these functions will be determined by either a 1) statistical norms reported from literature/experts (listed in decision matrix) based on a broad range of horses and/or 2) by a statistical study on a per horse basis. Either way, the statistics will generate parameters to be used to shape the input of the membership functions.

Figure 11:
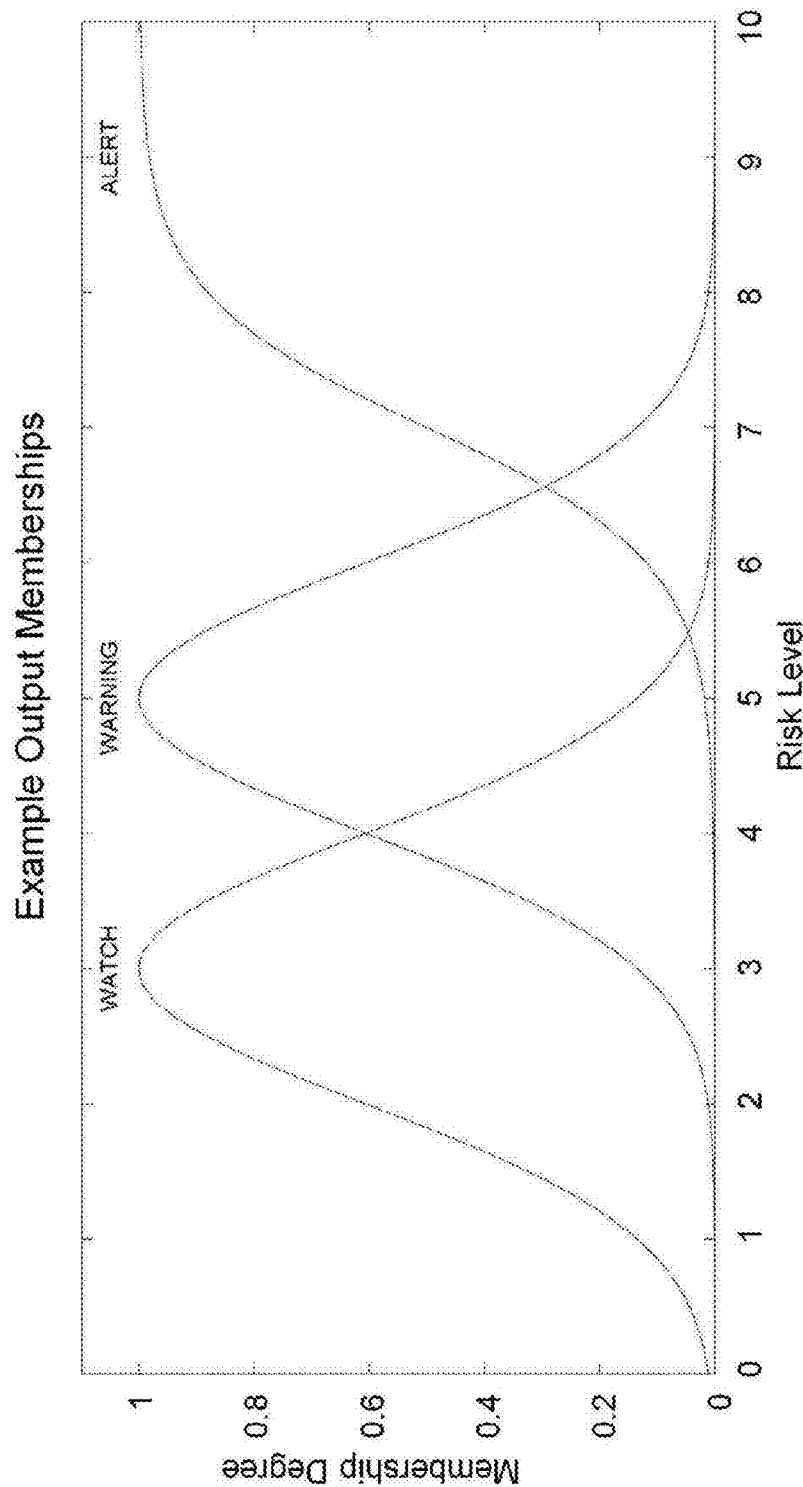
FIG. 11 is a graphical representation of output memberships for Watch, Warning, and Alert notifications.

Linguistically, the terms Critically Low (CL), Low (L), Below Normal (BN), Normal (N), Above Normal (AN), HIGH (H), and Critically High (CH) have been selected to related to the upper and lower thresholds for the predetermined three levels of distress that include Watch, Warning, and Alert. Output memberships for Watch, Warning, and Alert are created to serve as linguistic implications for various compositions of the inputs and membership functions. Examples of the output membership functions are shown in FIG. 11.

Fuzzy Rule Base

The fuzzy rule base for the biometric FIS has the potential to be generated by numerous rules considering there are three inputs each with seven input membership functions and three output membership functions. Only a few sample rules are provided. Three sample rules are provided below using Respiratory Rate (RR), Heart Rate (HR) and Body Temperature (Temp) along with the fuzzy database previously discussed.

Rule 1: If RR is HIGH Then Risk is WARNING
Rule 2: If HR is ABOVE NORMAL Then Risk is WATCH
Rule 3: If Temp is ABOVE NORMAL Then Risk is WATCH For these rules, only a single input was used per rule, but let it be noted that multiple inputs could be used. If multiple inputs are used then they need to be composed using the appropriate conjunctions such as shown in the following rules.

Rule 4: If RR is HIGH and HR is HIGH then Risk is WARNING
Rule 5: If Temp is HIGH or Temp is LOW then Risk is WARNING Inference For a given set of fuzzified biometric inputs, fuzzy rule base, and fuzzy database; inference for risk is calculated using a FIS. The output of the FIS is further defuzzified to provide a crisp assessment of biometric risk. For ease of explanation, the example fuzzy database and Rules 1-3 will be used to overview the FIS implementation.

There are several FIS design choices, but in hindsight of computational complexity those with less computation requirements have been selected. Larsen implication (algebraic product operator) and composition (max-product) has been selected due to computational advantages of algebraic product operator over the max operator. Graphical representation of the FIS implementation for the example rules can be seen in FIGS. 12-14.

Figure 12:
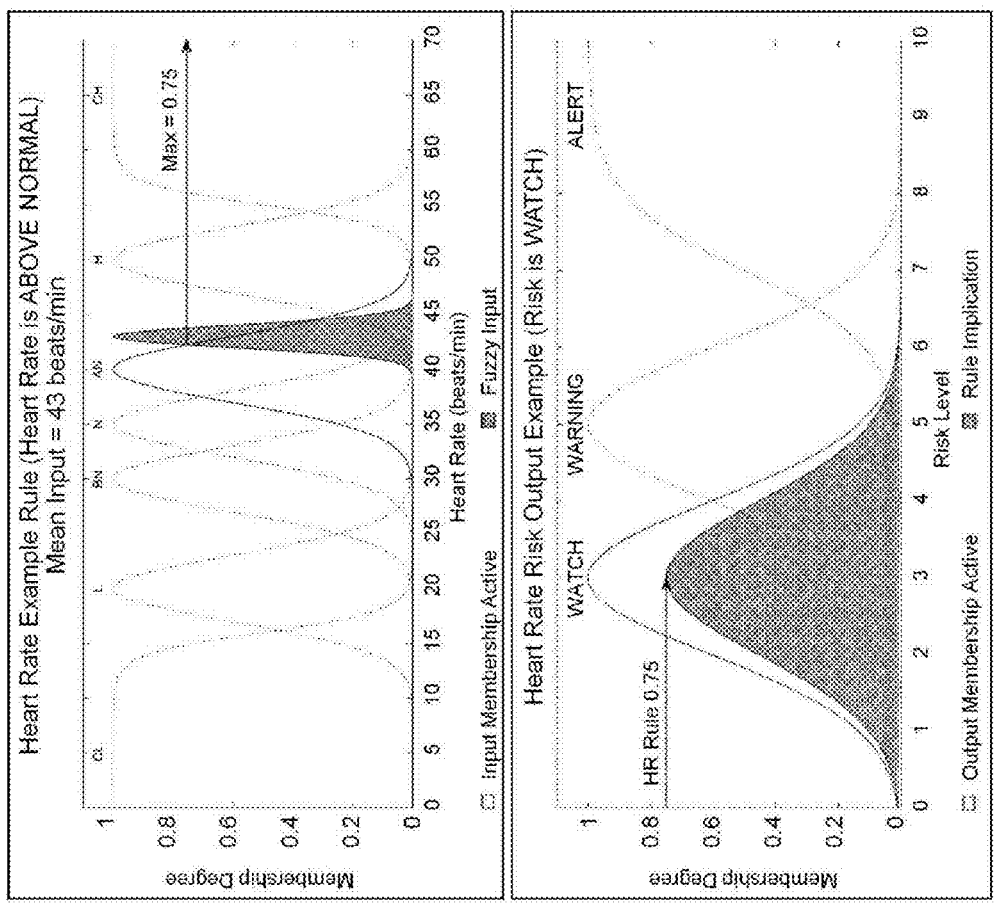
FIG. 12 is a graphical representation of FIS implementation using example fuzzy rules and database for heart rate.

With reference to FIG. 12, a graphical representation of the FIS implementation is illustrated for example rules for detecting heart rate.

Figure 13:
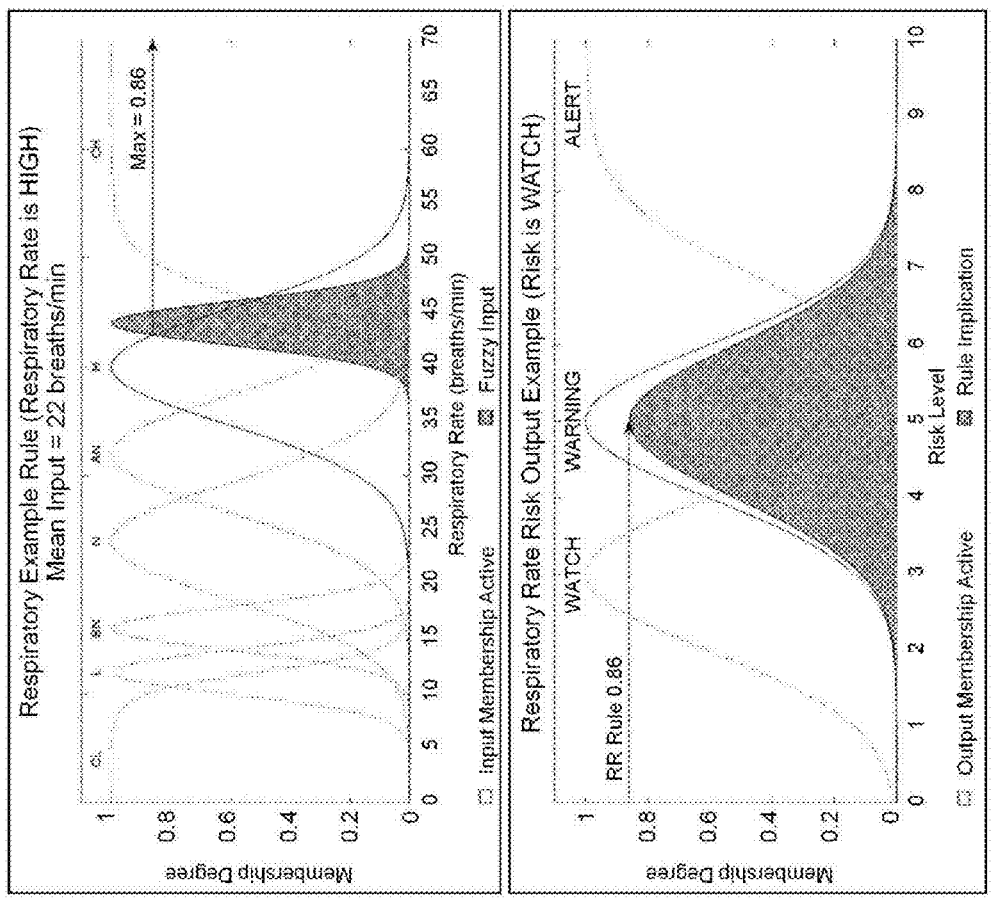
FIG. 13 is a graphical representation of FIS implementation using example fuzzy rules and database for respiratory rate.

With reference to FIG. 13, a graphical representation of the FIS implementation is illustrated for example rules for detecting respiratory rate.

Figure 14:
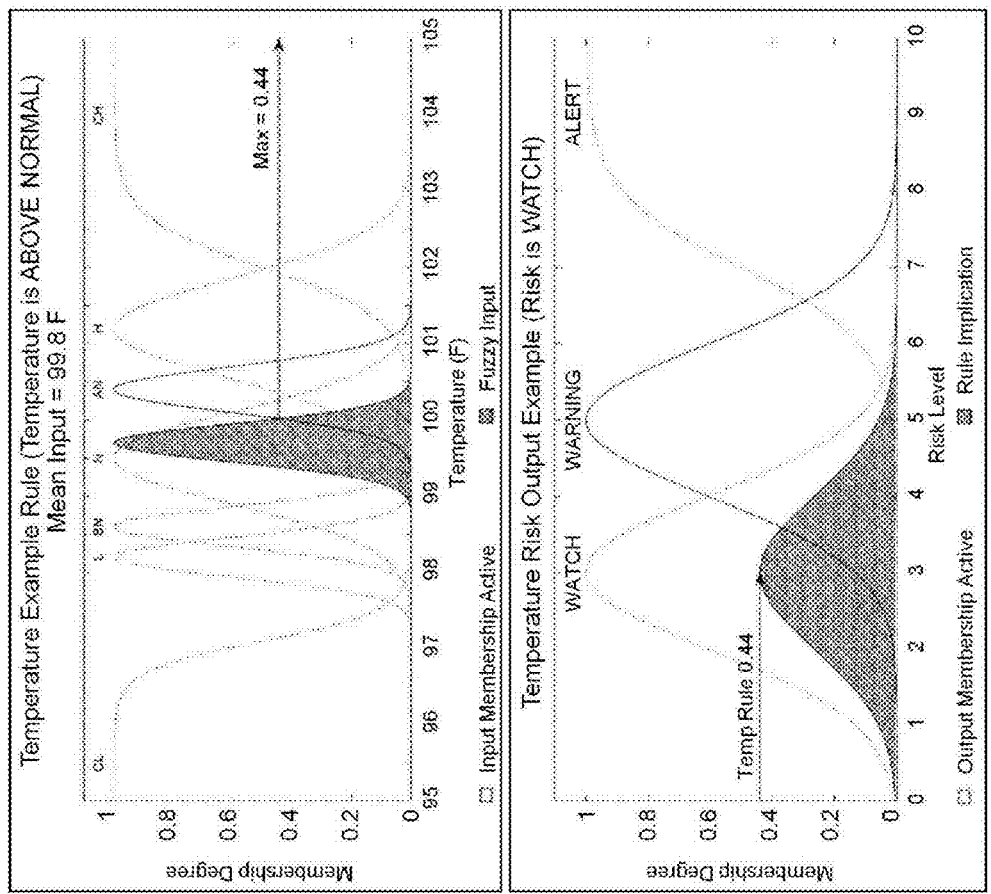
FIG. 14 is a graphical representation of FIS implementation using example fuzzy rules and database for temperature.

With reference to FIG. 14, a graphical representation of the FIS implementation is illustrated for example rules for detecting temperature.

Defuzzification

Figure 15:
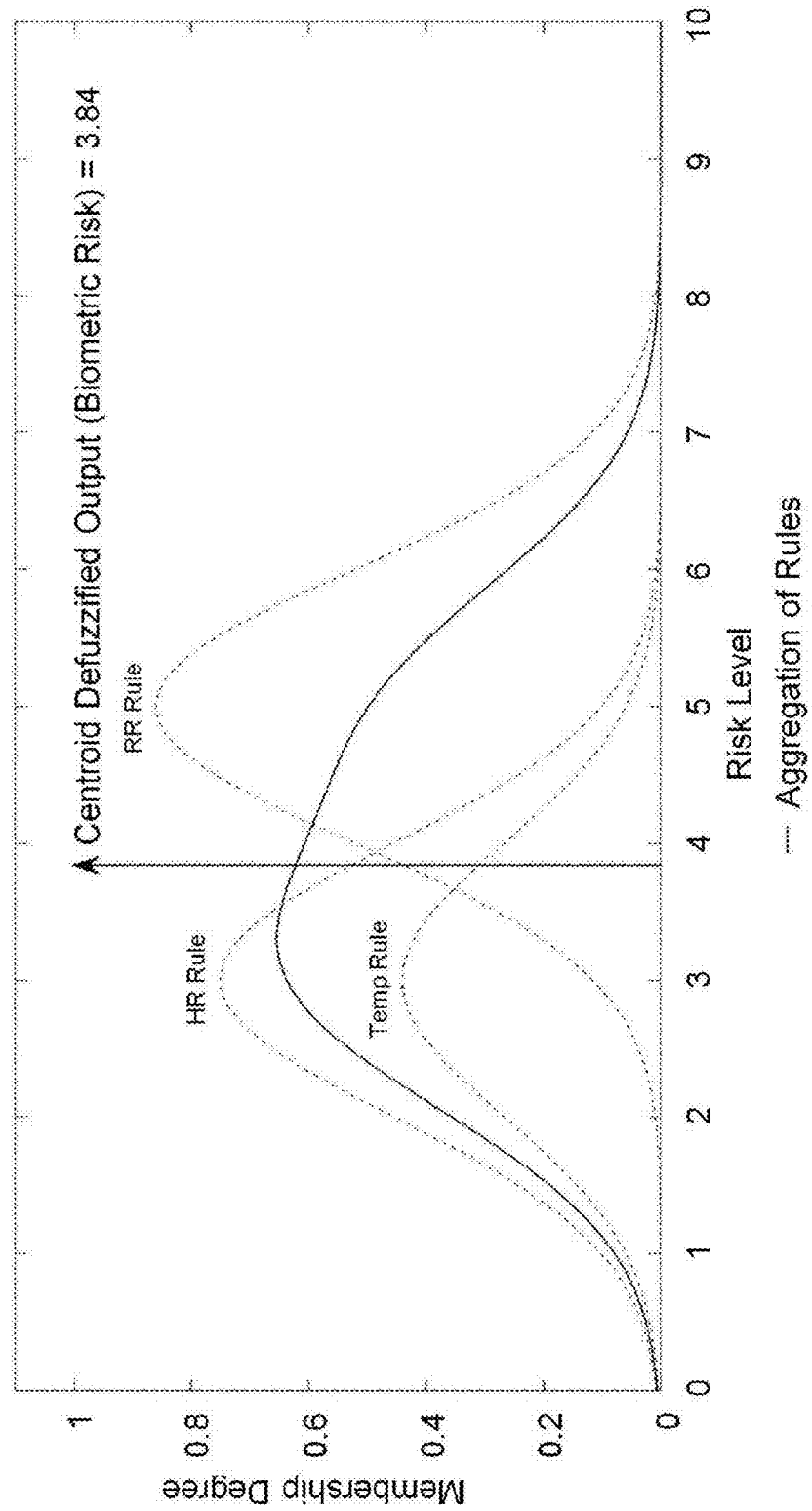
FIG. 15 is a graphical representation of biometric risk using example fuzzy rule aggregation and defuzzification.

Once all the rules are composed and implied to their corresponding outputs, the result is fuzzy sets in the form of Gaussians representative of each rule's influence on the output. The aggregation of all these rules needs to be defuzzified to generate a crisp value for biometric risk. For computational complexity reduction, the weighted averages defuzzification method is used. FIG. 15 shows the result of the aggregation of the rules and the final defuzzified output. For the three example rules and example inputs, the final inference is an assessment of a biometric risk value of 3.84.

Motion Sensors

A multi-axis sensor is actually a number of sensors combined together. A 9-axis sensor includes a 3-axis accelerometer, a 3-axis gyroscope, and a 3-axis magnetometer. This 9-axis sensor combines information provided by all of the sub-sensors to generate a dataset that describes in detail the movements of the monitored animal. A single-axis barometric pressure sensor captures the absolute altitude of the MASNS device and further represents another input for analysis.

When a horse is experiencing distress there are a number of movements they may enact instinctually in response. While different stressors can elicit different movements, the differentiation between these movements may also provide information as to the type of stressor that is affecting the animal. External stressors (e.g., presence of predators) may cause the horse to repeatedly spin in circles and buck, whereas internal stressors (e.g., abdominal discomfort) may cause the animal to repeatedly lie down/rise and roll with or without thrashing of its legs or presence of a healthy shake upon standing/rising. These characteristic motion patterns to internal stressors can assist in the diagnosis of certain conditions such as colic. Many of these physical movements/actions indicating a potential colic are observable through the use of the multi-axis motion sensor coupled with or without other motion sensors.

Behavior Algorithm

Figure 16A:
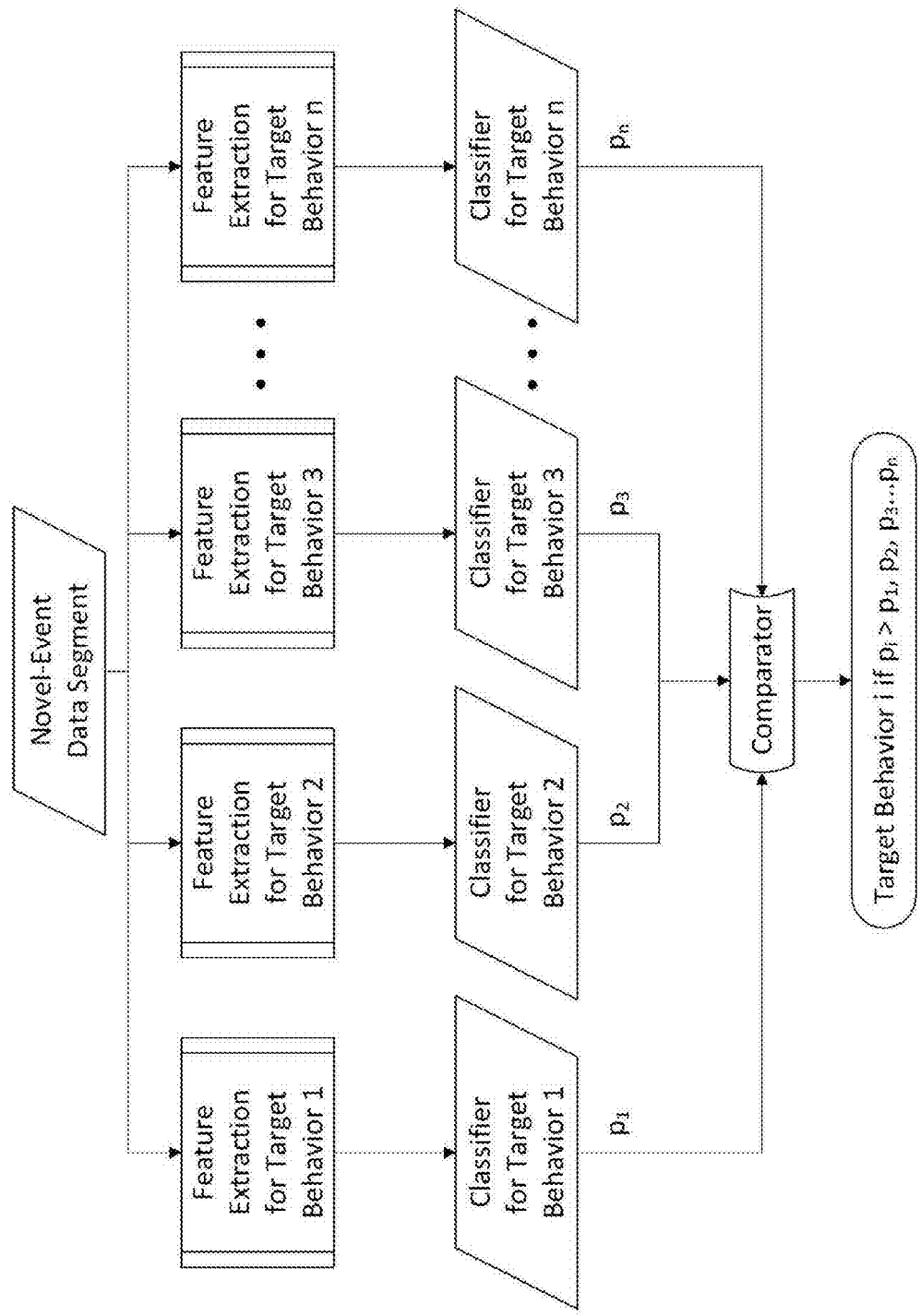
FIG. 16A illustrates one embodiment of a behavior algorithm.

With reference to FIG. 16A, the behavior algorithm is a classifier capable of cataloguing data segments using a classifier trained from expertly classified-data segments. During online operation of the behavior algorithm, data segments, which have been previously defined as novel, are provided to the algorithm. Thus, the behavior algorithm evaluates the data segments, which are marked as novel events by the NED algorithm. The NED algorithm determines the start and the end of the novel event and provides the corresponding data segment to the behavior algorithms. Each behavior algorithm is trained to identify a target behavior and outputs the probability of the novel event being the target behavior. Target behaviors can be categorized into different levels:

Primary: rise, fall, roll, lie down, no healthy shake, flank watch, paw, kick, etc.
Secondary: spin, flehmen response, bruxism, etc.
Tertiary: windsuck, crib, weave, etc.

As novel events happen rarely during the daily routine of the animal there will be limited number of samples (i.e., data segments). Thus, classifiers (i.e., one-class classifiers) used in the NED algorithm cannot be directly used, as there will not be enough statistics to calculate mean and standard deviation of the samples. However, an expert may select these parameters for a one-class classifier such that the successful classification can be done. Another possibility is to use classifiers where limited data can be accommodated such as Radial Basis Function Networks ("RBFN") and neural networks. RBFN are feed-forward neural networks where a layer of N basis functions (commonly Gaussian functions). The weighted sum of the outputs of the basis functions is the output(s) of the RBFNs. For a given data set and chosen mean and standard deviations for the Gaussian basis functions, the weights of the output layer can be learned. When there is enough statistics, the training samples are clustered and mean and standard deviations of the clusters are assigned to be the parameters of the Gaussian basis functions. As the novel events will be rare, RBFN with fixed parameters will be more suitable to learn a generalized model for a specific target behavior. However, with sufficient statistics, the parameters of the RBFNs can be calculated from the training samples. FIG. 16B presents the flow diagram for a behavior classifier for a specific target behavior.

Novel-Event Detection (NED)

NED provides the capability of identifying and classifying novel data segments, or windows, contained in a series of semi-continual data samples. A novel window is one that has any new or unknown information that was not used or was not available during algorithmic training. Each window is composed of samples of motion sensor data. During training, a model is created to represent the sensor data during normal conditions. For this application, normal conditions are defined as periods of activity without motion behaviors that may be indicative of distress. Thus, the model created during the training process is referred to as the normal model. During online operation, windows of motion data are sequentially provided to the NED algorithm. Each window is compared against the trained normal model and classified. Those windows that are rejected by the normal model are classified as novel and their data and time information become candidates for further analysis. Contiguous novel windows are then grouped together and defined as a novel event. A novel event is capable of providing indicators for stress-related behaviors that cannot be contained within a single window.

NED Algorithm

Figure 17A:
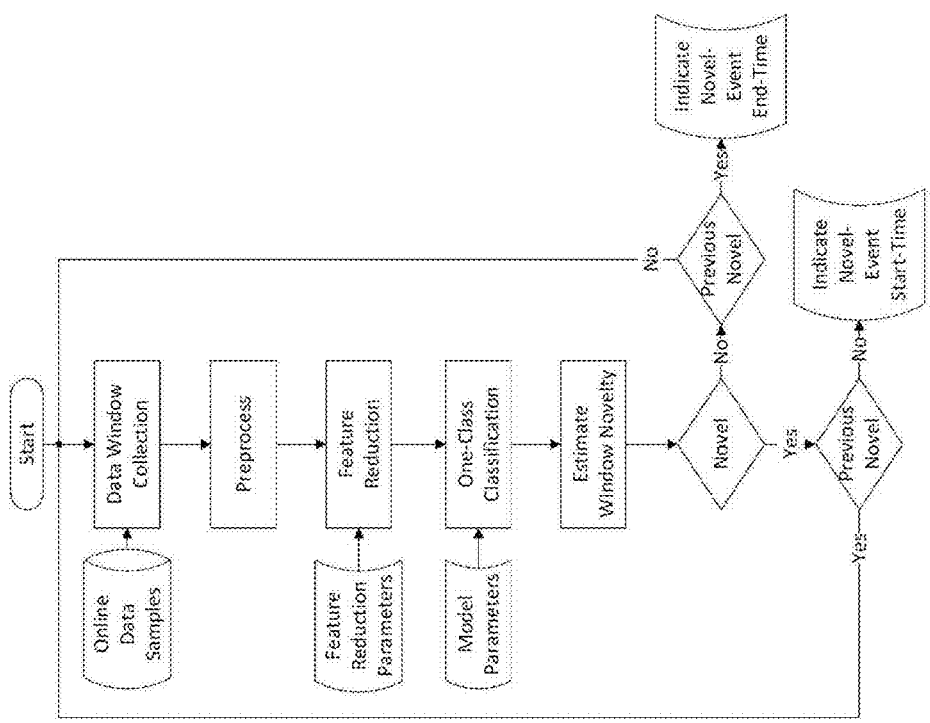
FIG. 17A illustrates one embodiment of NED with one-class classification.

With reference to FIG. 17A, the NED process is continually running while the system is in an active data collection mode. This process begins by obtaining the most current window of raw motion data from the Data Window Collection process (implementing any preselected algorithmic or model parameters). After a window of data is obtained, it is preprocessed to convert the window into a feature vector. This feature vector is further reduced in size and used in a one-class classifier. The one-class classifier compares the feature vector to a normal model and provides a binary decision of "normal" or "non-normal." Non-normal indicates that the current feature vector is rejected by the normal model. Once a window is determined as normal/non-normal its novelty is estimated based on previous windows' classifications. If the window is determined as novel its data and time information are stored.

Each of the NED procedures is listed below with additional high-level details.

1. Data Window Collection

This process involves the windowing of the raw motion data from the sensors. The output of the Data Window Collection process is the most recent window of raw motion data.

2. Preprocessing

After collecting the most current window of raw motion data, this window is converted into a format more suitable for classification. During preprocessing, the time-based motion is filtered to remove noise, transformed into the frequency domain, and the power of individual frequency bands computed. These powers of frequency bands are used to generate the feature vector.

i. Filter—To filter high frequency noise from the filter a low-pass Butterworth filter is used.

ii. Frequency Transformation—Each sensor's data within the window is transformed using the Fast Fourier Transform ("FFT") to obtain coefficients relative to frequency components of each sensor's raw data.

iii. Band Power—The absolute value of each sensor's FFT coefficients is used to represent the power of the individual frequencies. Neighboring frequencies' powers are combined to determine the power within bands of frequencies.

iv. Feature Vector Creation—The feature vector is created by concatenating the frequency power bands from all the sensors into a single vector.

3. Feature Reduction

The feature vector is further reduced based on feature reduction parameters that were learned during the Model Learning process.

4. One-Class Classification

For one-class classification, the reduced feature vector is input into the normal model that was generated during the Model Learning process. The model itself is a Gaussian Mixture Model ("GMM") that was learned to represent sensor data under normal conditions. The output of the mixture model is a probability that the input vector belongs to the model also referred to as likelihood. If the likelihood is lower than a set threshold value the feature vector is rejected from the model.

5. Estimation of Novelty

Even though a window may be classified as non-normal, it may not indicate that the window is a part of a novel event. The current window's novelty is estimated using previous windows' normal/non-normal classifications. This is done to help reduce the number of false positives that the system may produce.

NED Data Window Collection

Figure 17B:
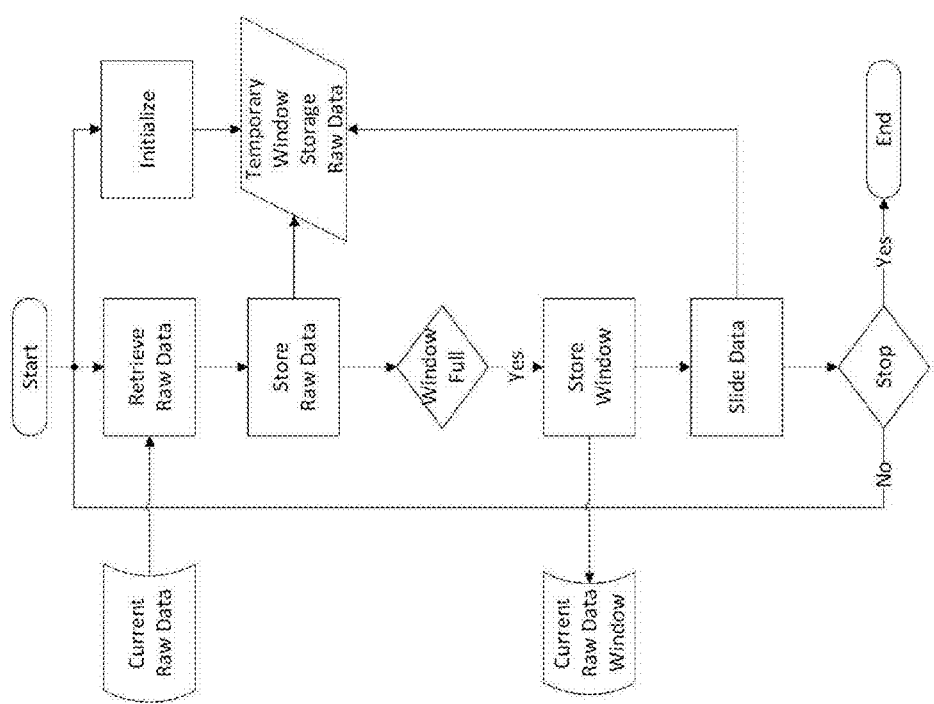
FIG. 17B illustrates one embodiment of NED data window collection.

With reference to FIG. 17B, the process of windowing the raw motion data collected from the sensors is described. The flow is essentially the realization of sliding window data collection. The system is continually sampling data from the motion sensors and the purpose of the data window collection process is to buffer and shift the sampled data in preparation to be provided to other processes such as the NED algorithm or Model Learning process. The Data Window Collection process is continually running while the system is actively collecting data.

NED Model Learning

Figure 17C:
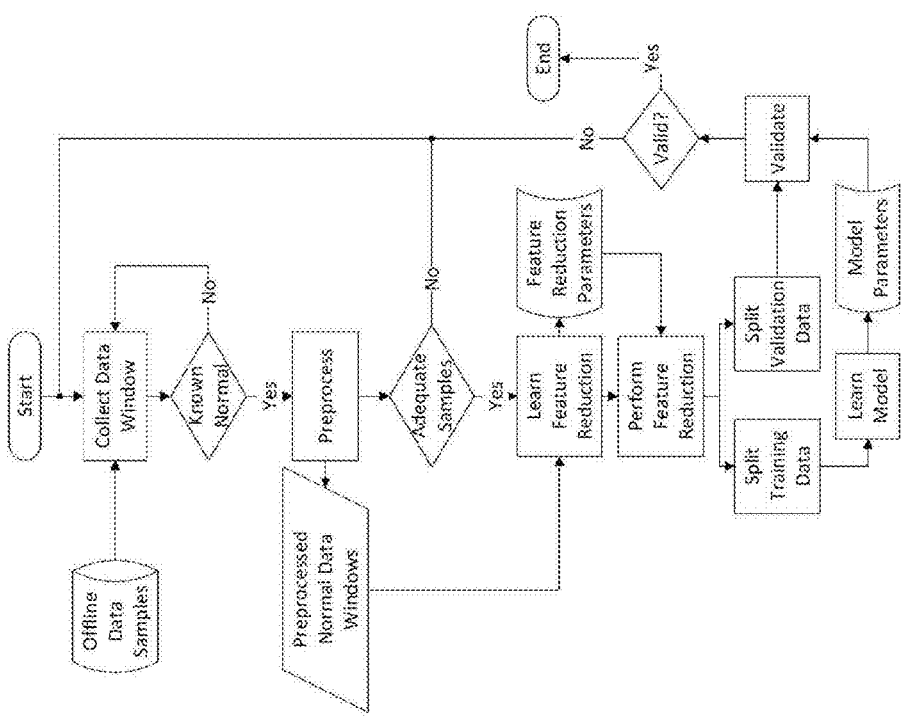
FIG. 17C illustrates one embodiment of NED model learning.

With reference to FIG. 17C, the model learning procedure is one that is preformed offline from the actual system itself. The purpose of the model learning process is to generate a model that represents sensor data during normal conditions. It has been previously stated that normal is defined as periods of activity without motion behaviors that may be indicative of distress. During the learning process data is collected from stored field data; stored data allows for offline processing. The learning process uses the same data collection and preprocessing techniques as seen in FIG. 17A.

The overall offline procedure for model learning begins by collecting stored data samples from known normal conditions. The raw data samples are prepossessed to generate feature vectors to be used in model creation. The feature vectors are then used to learn a Principal Component Matrix ("PCM") to be used for future feature reduction. The features are reduced using the learned PCM. The reduced features are split into training and validation subsets, where the training data is used to train the model and validation used to validate the model. Using the training feature vectors, a GMM is learned using the Expectation Maximization ("EM") algorithm. The learned model is applied to the validation feature vectors and the fitness of the model is compared to that of the training fitness. If the fitness values are similar than the model learning process is complete otherwise it must be repeated with different data.

Each of the procedures is listed below with additional high-level details.

1. Data Collection

Same process discussed in NED algorithm. The only difference for data collection during model learning is that only normal data is used. Therefore, any window of raw data that contains a previously known event is not included in the dataset for learning.

2. Preprocess

Same process discussed in NED algorithm.

3. Learn Feature Reduction

The feature reduction process uses Principal Component Analysis ("PCA"), which is a method of projecting data in to a smaller principal component space. The specific PCA method done was that as defined by Alpaydin (*Ethem Alpaydin. Introduction to Machine Learning. The MIT Press, Cambridge, Mass., second edition,* 2010). PCA during the model learning process is applied to all the data windows selected for learning and these learning windows are only from data segments know to be from normal conditions. After applying PCA to the learning set, a PCM is determined. This PCM may be used to reduce the dimensionality of the feature vector to contain a smaller subset of features that are statistically significant enough to explain the learning dataset.

4. Perform Feature Reduction

The learned PCM is used to reduce all of the feature vectors for learning.

5. Split Data

The reduced learning feature vectors are split into two groups. One group is for training the model and the other is used to validate the model. This process is very common and its purpose is to check for overtraining of the model and essentially robustness of the model.

6. Learn Model

The model used is a GMM, which is a probabilistic model and is used to represent the sensor data under normal conditions. The actual derivation and implementation of a GMM is in accordance with McLachlan and Peel (*Geoffrey McLachlan and David Peel. Finite mixture models.* John Wiley & Sons, 2004). To learn the model parameters the EM algorithm is used. EM is a commonly used method to estimate model parameters for a mixture model, especially targeting Gaussian mixtures. The specific implementation of EM used is one published by Verbeek et al (J J Verbeek, N Vlassis, and B Krose. *Efficient greedy learning of gaussian mixture models. Neural computation,* 15(2):469-85, February 2003).

During the learning process, the preprocessed and reduced training feature vectors are used in the EM algorithm. EM learns the GMM parameters including means, covariances and weights. The number of mixture components is preselected based on empirical trials. After the model is learned, the training feature vectors are input into the model to get their likelihood of belonging to the learned model. One-class classification is applied to likelihoods to get a quantitative result of the fitness of the model.

7. Validate Model

To validate the model, the validation data is applied to the learned model, likelihood values obtained, and one-class classification performed. The result of the one-class classification from the validation data is compared to the result from the training data. If these results are reasonably close then the model training is complete. In the event that the training and validation results are not close, the whole model process will need to be repeated using a better training set of data.

The aforementioned procedure can be reapplied on a per animal basis at any given time and repeated infinitely to adapt and configure the system for each specific animal (i.e., data from a robust set of incidences on an individual animal vs. robust data from a sample population of multiple representative animals).

Biometric and Biologic Sensors

The MASNS contains biometric and biologic sensors capable of monitoring physiological parameters of a horse, including but not limited to heart rate, respiratory rate, temperature, and digestive sounds. When encountering a stress (e.g., colic, being cast, foaling) a horse will have certain physiological responses such as the release of adrenaline, which gets their body ready for a fight-or-flight response. This fight-or-flight response can be seen in all mammals and evidenced by an increase in heart rate and blood pressure so they can be best prepared to respond to the stress-inducing stimulus. A horse's heart rate (i.e., pulse), along with other vital signs (i.e., respiratory rate and body temperature) and biologic functions (i.e., digestive sounds), serve as surrogates for a horse's overall physiological state, and therefore represent useful targets for monitoring distress in horses.

The system in this disclosure is able to monitor known physiologic responses to stress through the use of biometric and biologic sensors. The horse's pulse (normal range of about 30-40 beats per minute) is monitored through the use of an UWB-IR and a TIRS; the horse's respiratory rate (normal range of about 8-16 breaths per minute) is monitored through the use of an UWB-IR and a microphone; the horse's body temperature (normal range of about 98.6°-100.4° Fahrenheit; slightly higher in foals and warm weather) is monitored through the use of an TIRS; and the horse's digestive sounds (normal characteristic sounds are rumbling and gurgling no less than every 10-20 seconds vs. sloshing or inaudible/faint sounds lasting more than about 1 minute) is monitored through the use a microphone.

The MASNS constantly monitors these vital signs and biologic functions in the animal, and runs the real-time data through algorithms to determine if there is sufficient indication of distress in the animal to warrant alerting the animal's caretaker(s). If, after the MASNS has processed these physiologic and other data inputs, the system has determined that there is sufficient evidence that the animal is experiencing an abnormal amount of distress, it will trigger a notification.

It is important to note that, in horses, some of the physiologic responses to stress can be mirrored by normal responses to situations when the animal is not in a distressed state. For example, a horses' heart and respiratory rates will increase when the horse is simply running. As such, the biometric data being processed by the MASNS comprises one of many parameters that the system analyzes in order to determine whether or not the animal is in a stressed state or not.

Biometric Algorithm

Figure 18:
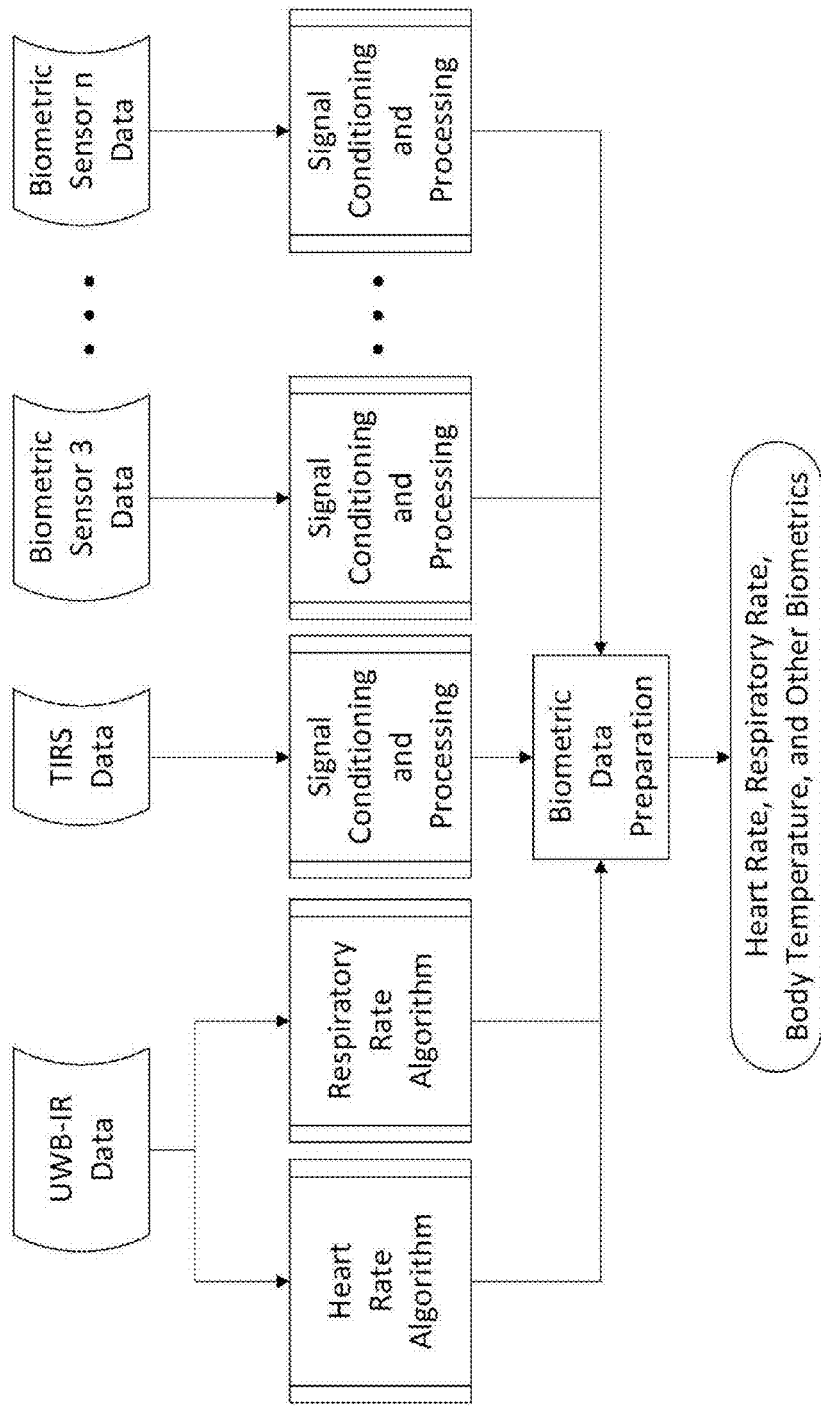
FIG. 18 illustrates one embodiment of a biometric algorithm.

With reference to FIG. 18, the biometric algorithm is a collection of signal processing algorithms for determining biometrics of an animal. Biometrics are values that describe specific anatomical condition/rate of the horse such as heart rate, respiratory rate, and temperature. Thus, any biometric gathered from an animal presents information regarding the health of the equine and can be analyzed by a veterinarian or a system.

Sensors can provide data in two ways (1) a sensor that provides the biometric value directly, such as TIRS; (2) a sensor that provides raw data for a specific biometric value to be calculated, such as UWB-IR. In the case of a sensor that provides the biometric value directly, only signal conditioning and signal processing is needed. In the case of a sensor providing raw data, there is a need for a detection algorithm for each biometric value. In FIG. 18, respiratory rate detection algorithm and heart rate detection algorithm are specifically designed to calculate respective rates. The final stage of the biometric algorithm is biometric data preparation where these values are prepared to be integrated into the MASNS decision-making protocol as depicted in FIG. 3

Respiratory Rate and Heart Rate Algorithms

Figure 19:
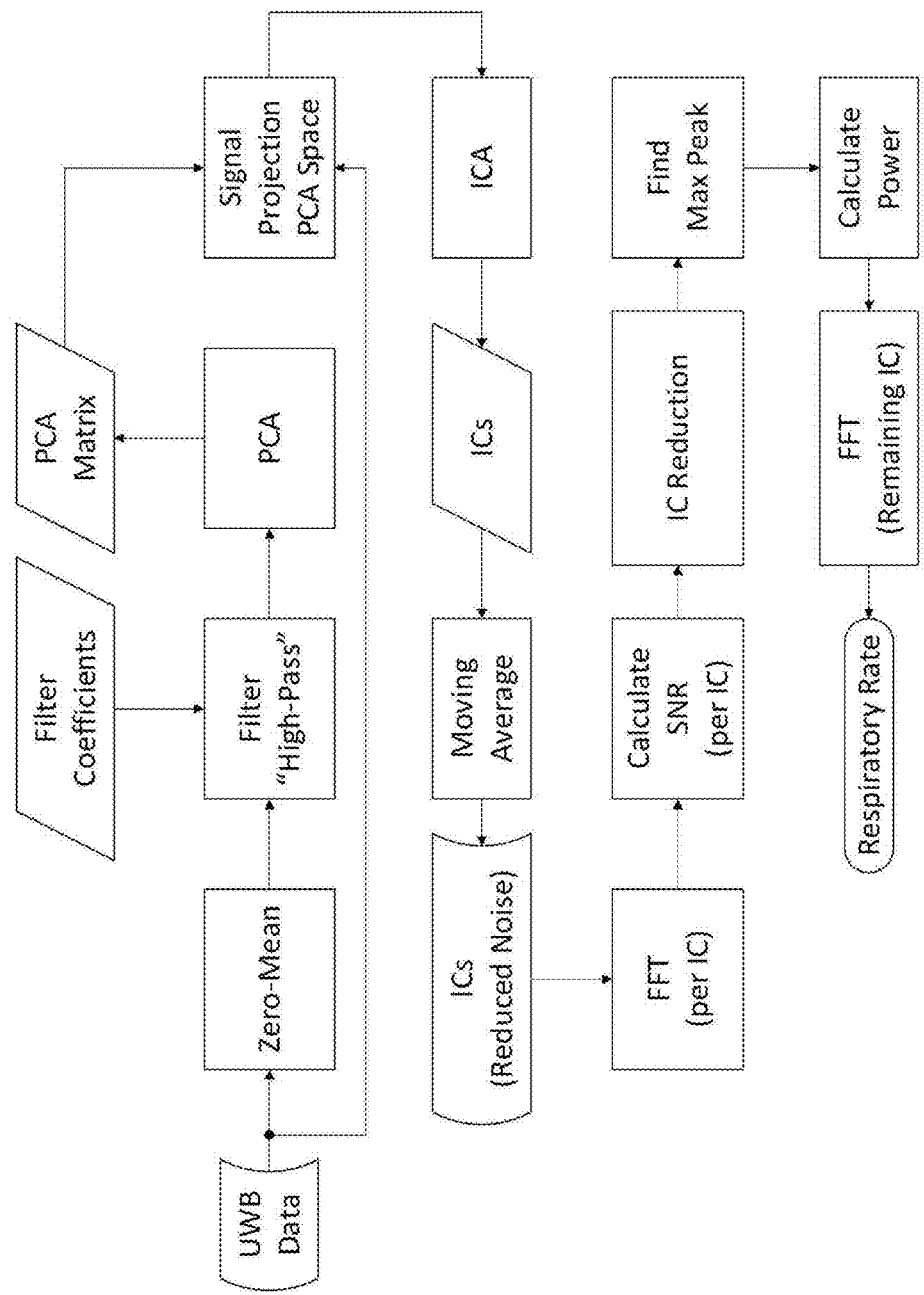
FIG. 19 illustrates one embodiment of a respiratory rate algorithm.
Figure 20:
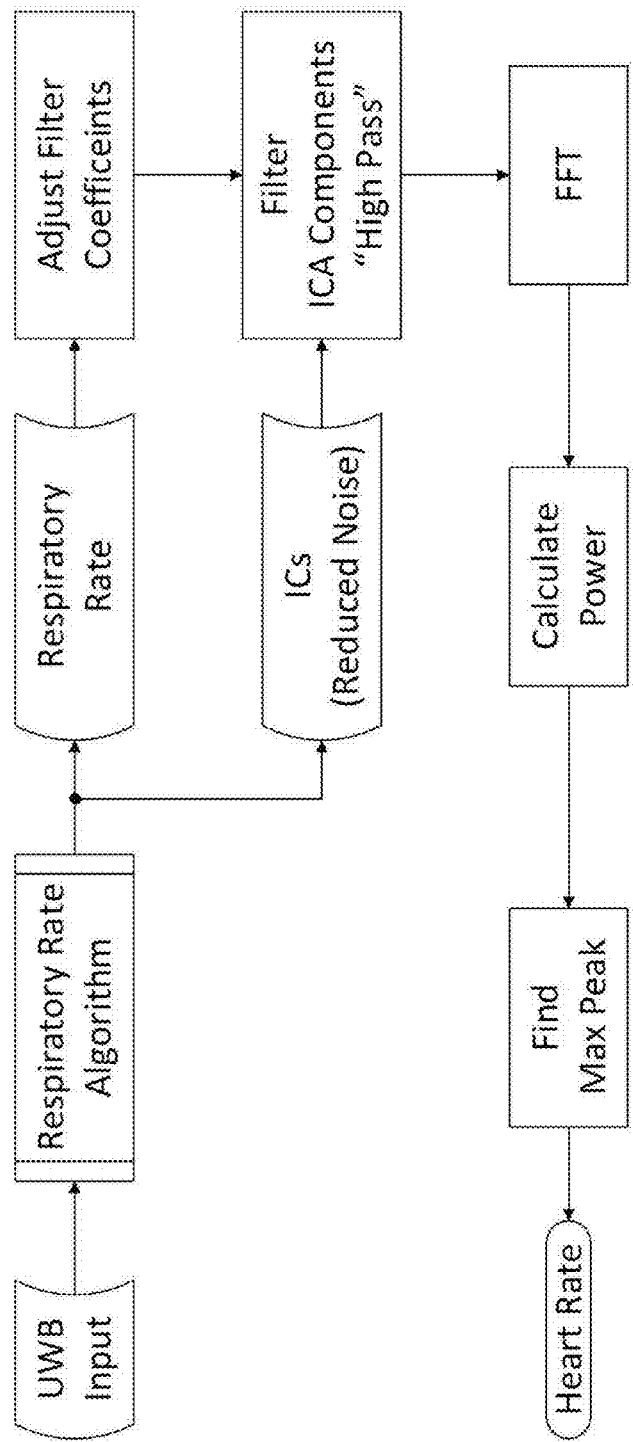
FIG. 20 illustrates one embodiment of a heart rate algorithm.
Figure 21A:
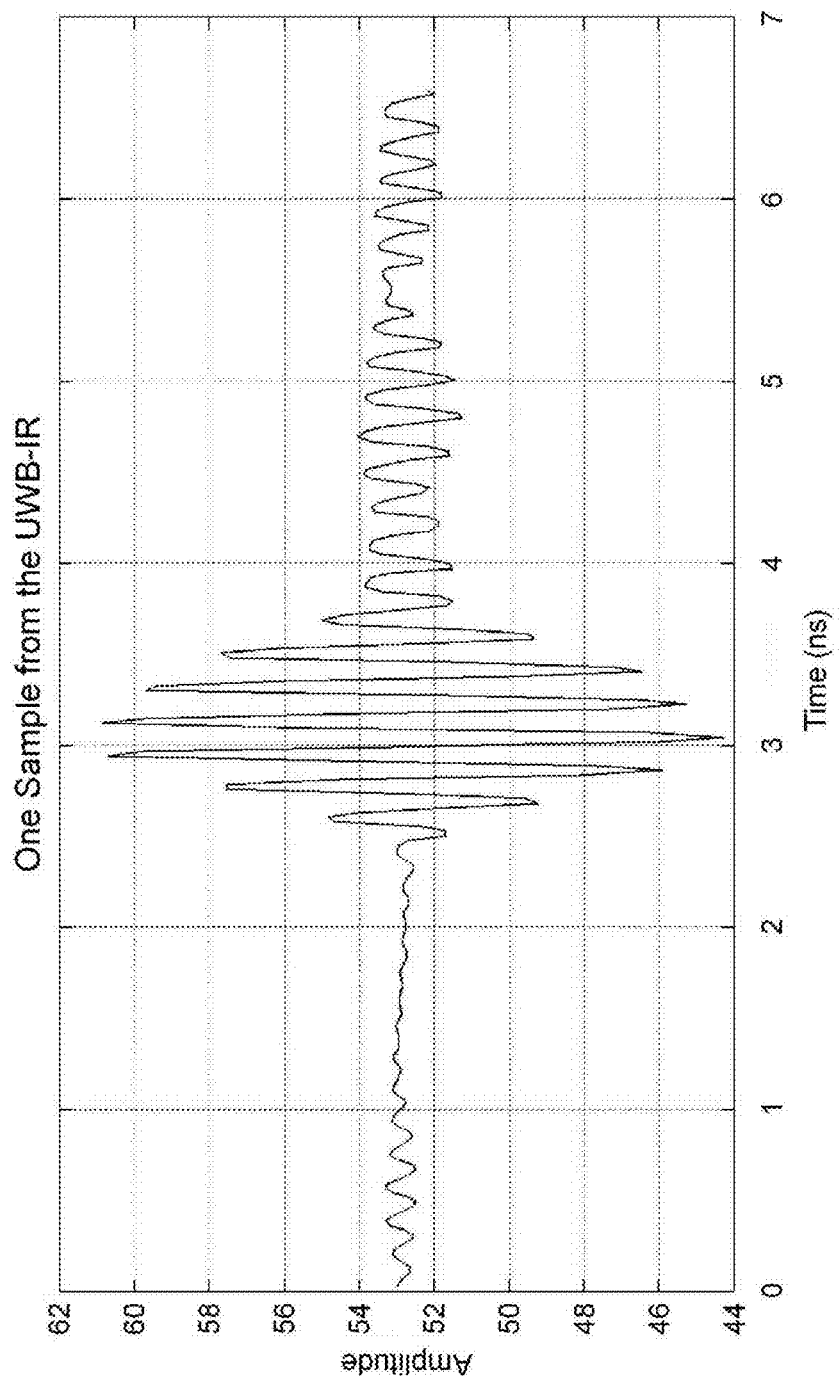
FIG. 21A illustrates one embodiment of a respiratory rate algorithm with one reading from a UWB-IR device.
Figure 21B:
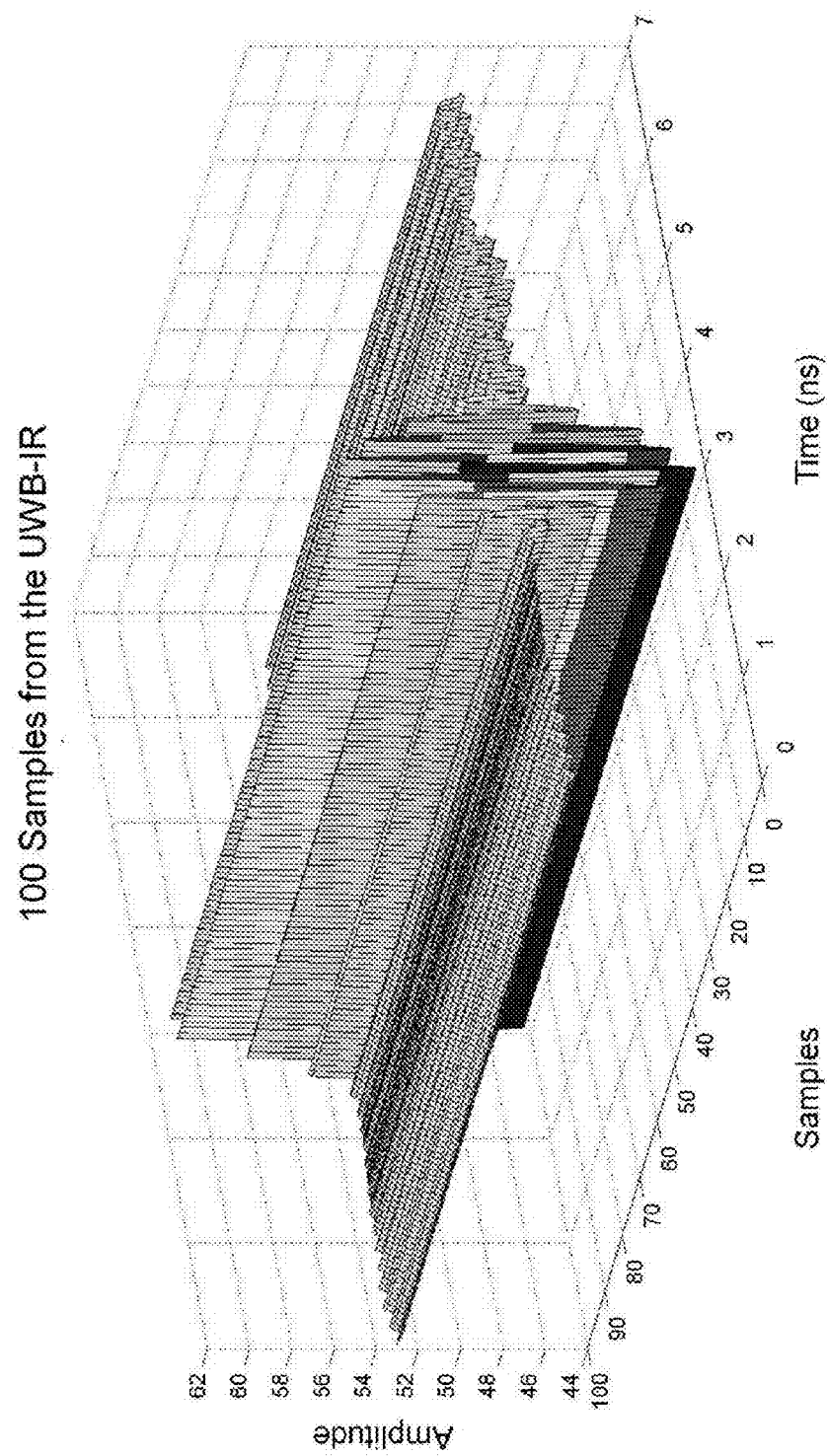
FIG. 21B illustrates one embodiment of a respiratory rate algorithm with 100 samples from a UWB-IR device.
Figure 21C:
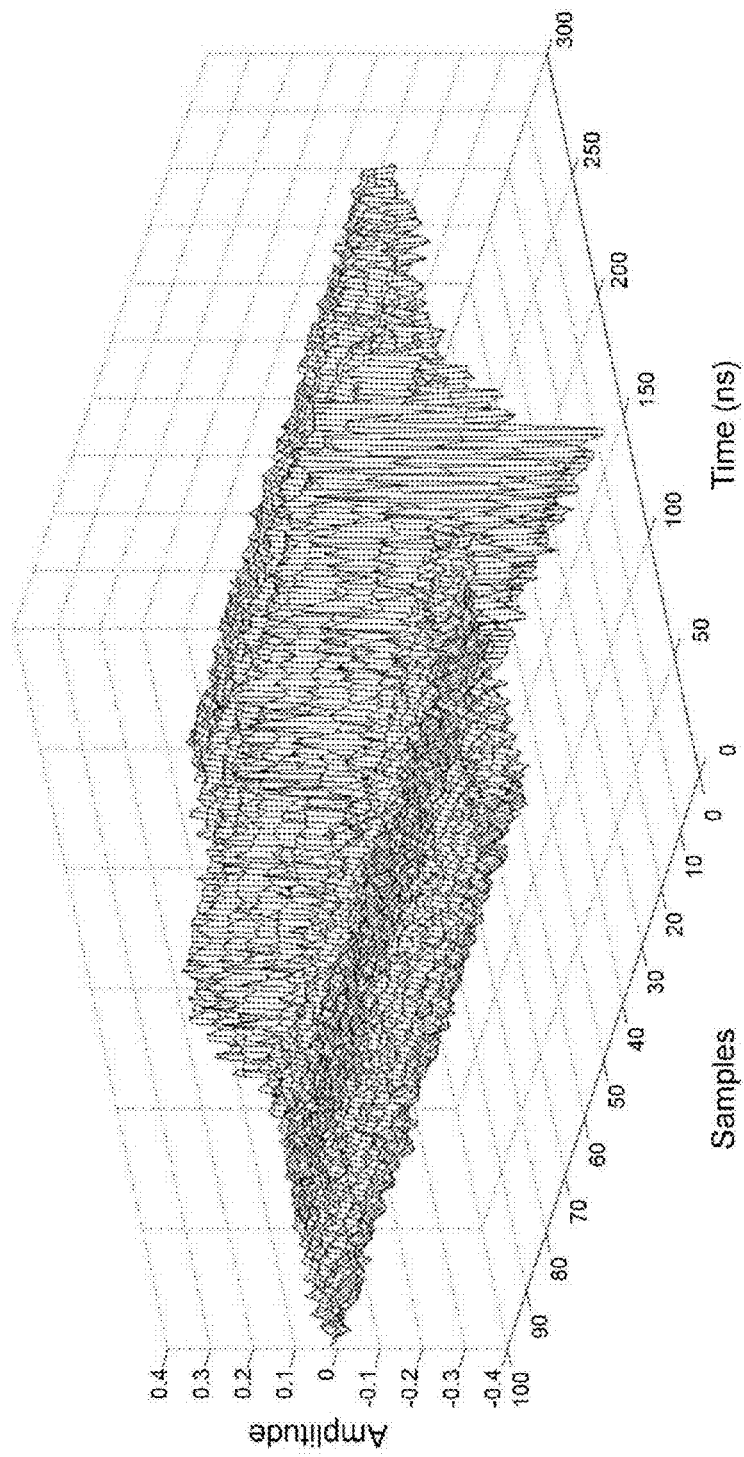
FIG. 21C illustrates one embodiment of rhythm data after filtering and zero mean.

The respiratory and heart rates are determined by analyzing data provided by an UWB-IR. Respiratory rate and heart rate algorithm flow charts are illustrated in FIG. 19 and FIG. 20 respectively. The UWB-IR provides times of flight of radio frequency signal for a specific range. FIG. 21A shows one reading of an UWB-IR sensor. The sensor scans 1-meter range for 6.6 ns. FIG. 21B shows 100 samples in time of such readings as an illustration as a new sample is provided in approximately 250 ms. FIG. 21C presents the result of an initial signal processing of the UWB-IR readings ("rhythm data") using a "high-pass" filter and removal of the mean in the sample scale. By removing the mean in the sample scale, the motion in the object can be seen for a given distance.

After removing the mean and cleaning the rhythm data, PCA is applied to the rhythm data in order to determine the principle (i.e., important) components of the data. By keeping most of the information in the data, PCA maps the rhythm data in a smaller space, in FIG. 21D, this is given as eight components. Thus, a reduction of the number of variables in data is from 256 to 8. PCA generates orthogonal principle components that have similar variance. Thus, the PCA keeps important information and removes the noise component from the signal in a compact form.

Figure 21D:
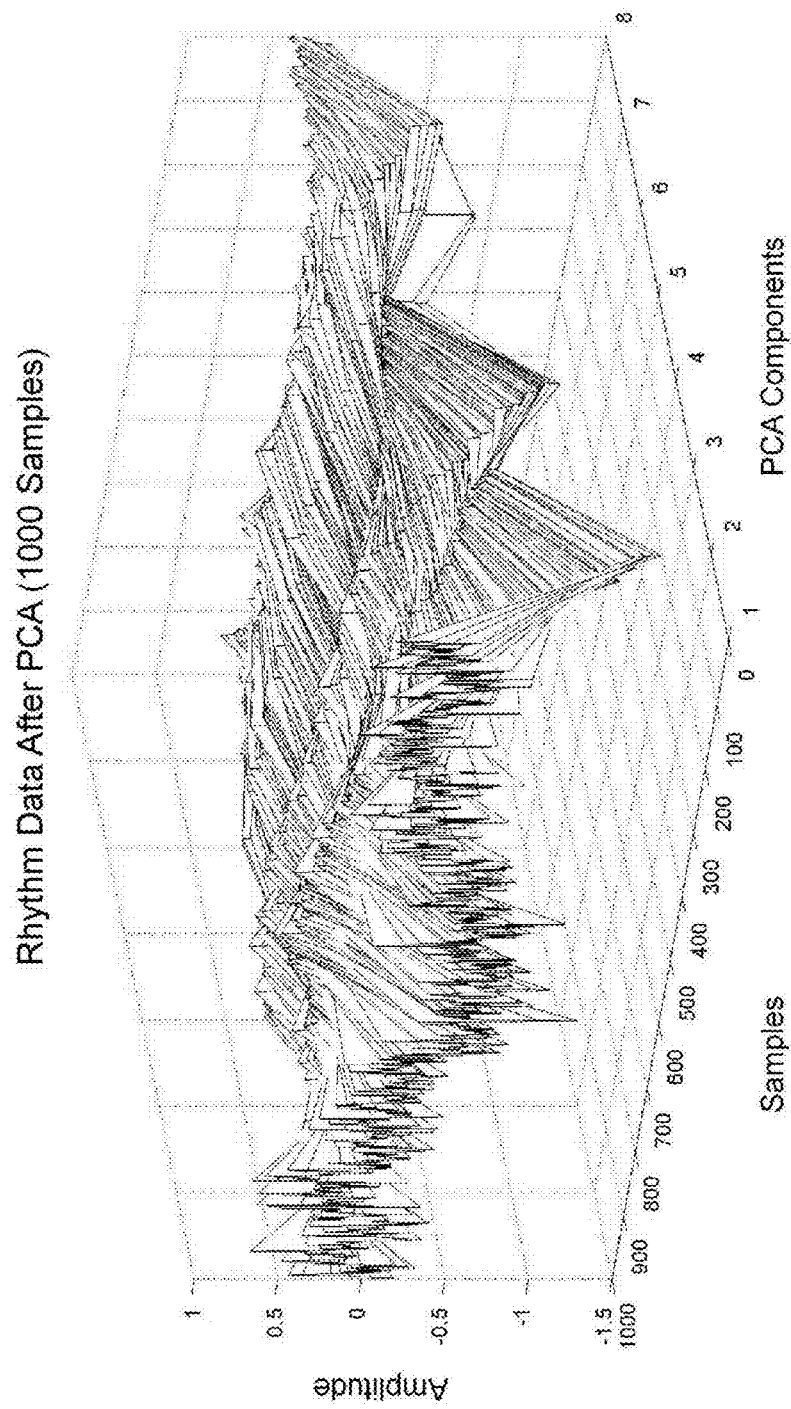
FIG. 21D illustrates one embodiment of PCA components of rhythm data.
Figure 21E:
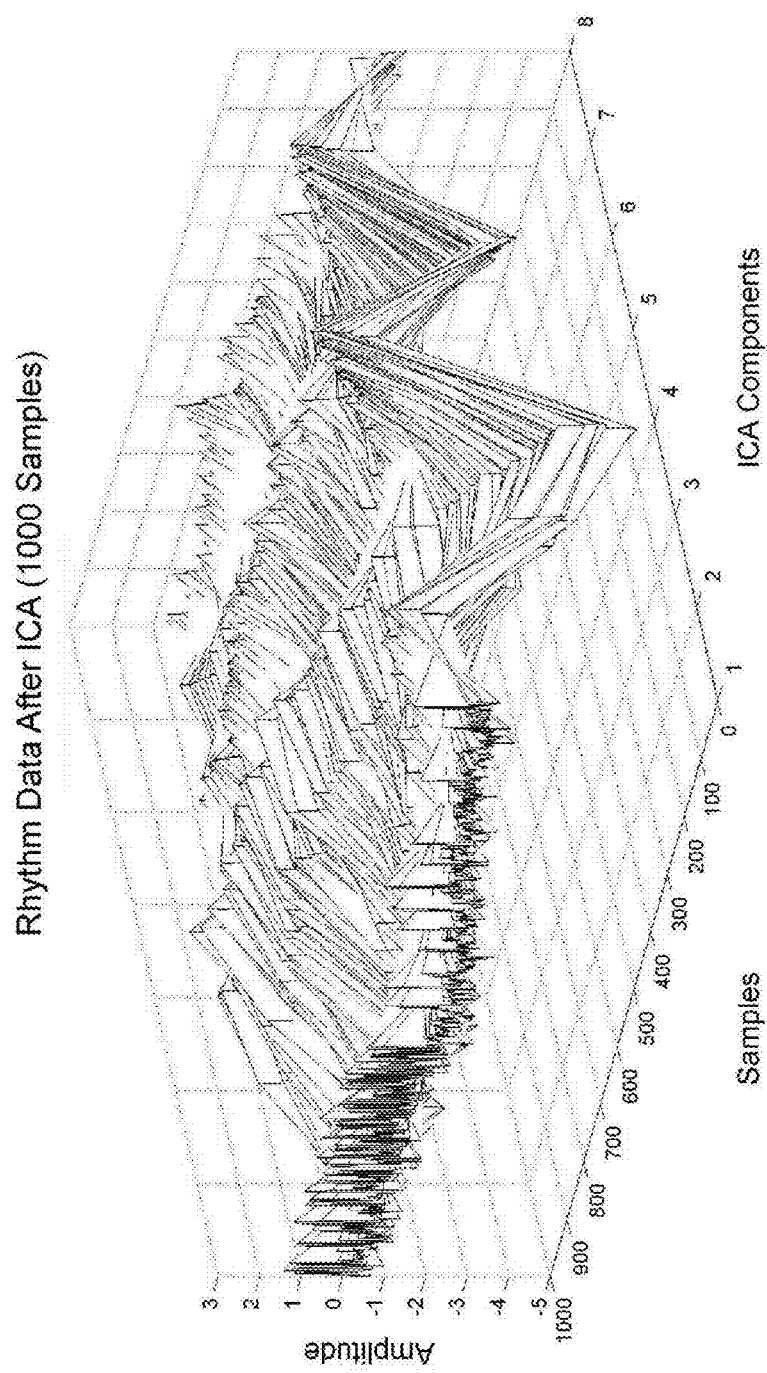
FIG. 21E illustrates one embodiment of ICA components of rhythm data.
Figure 21F:
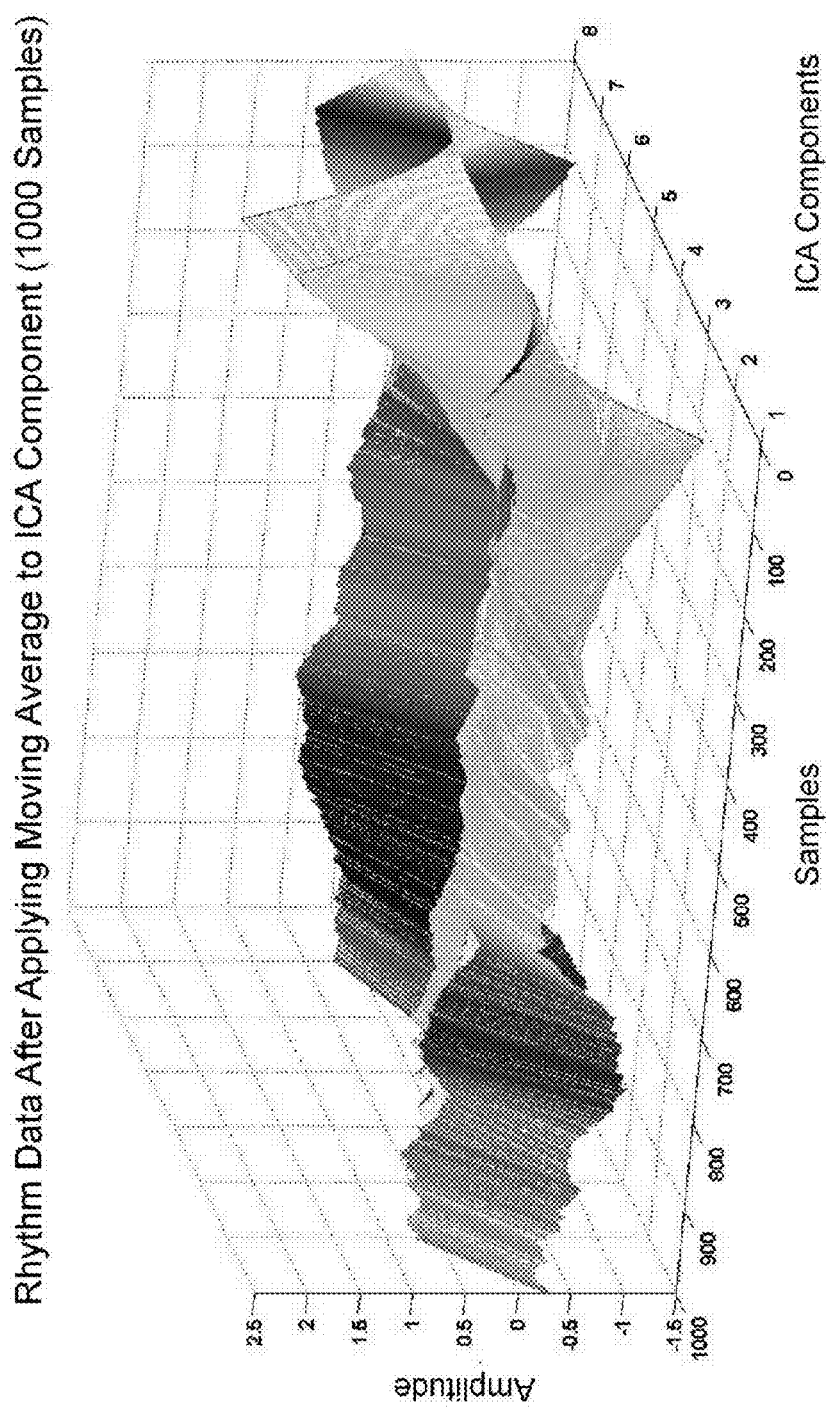
FIG. 21F illustrates one embodiment of smoothened ICA components of rhythm data.

After the PCA, an Independent Component Analysis ("ICA") is performed in order to determine independent components of the signal so that the same information is not repeated in the signal. FIG. 21E shows eight ICA components calculated from the PCA components calculated in the previous step. After applying ICA, the rhythm data is represented in a compact form where the variables have independent and important information. FIG. 21F shows the ICA components after applying a moving average in order to remove high frequency components and smoothen the ICA components for a better frequency analysis.

Figure 22A:
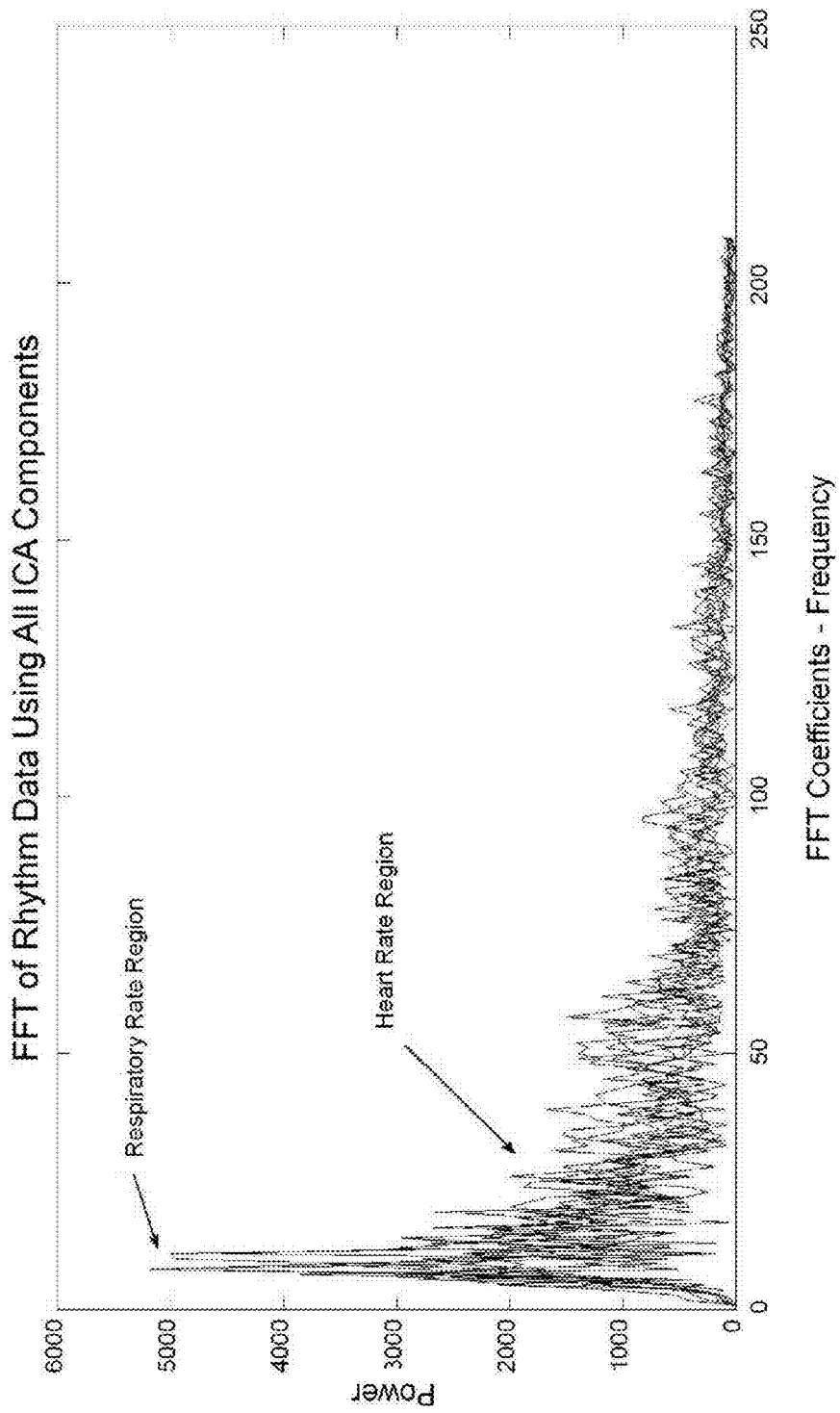
FIG. 22A illustrates one embodiment of 2D FFT analysis of rhythm data using all ICA components.
Figure 22B:
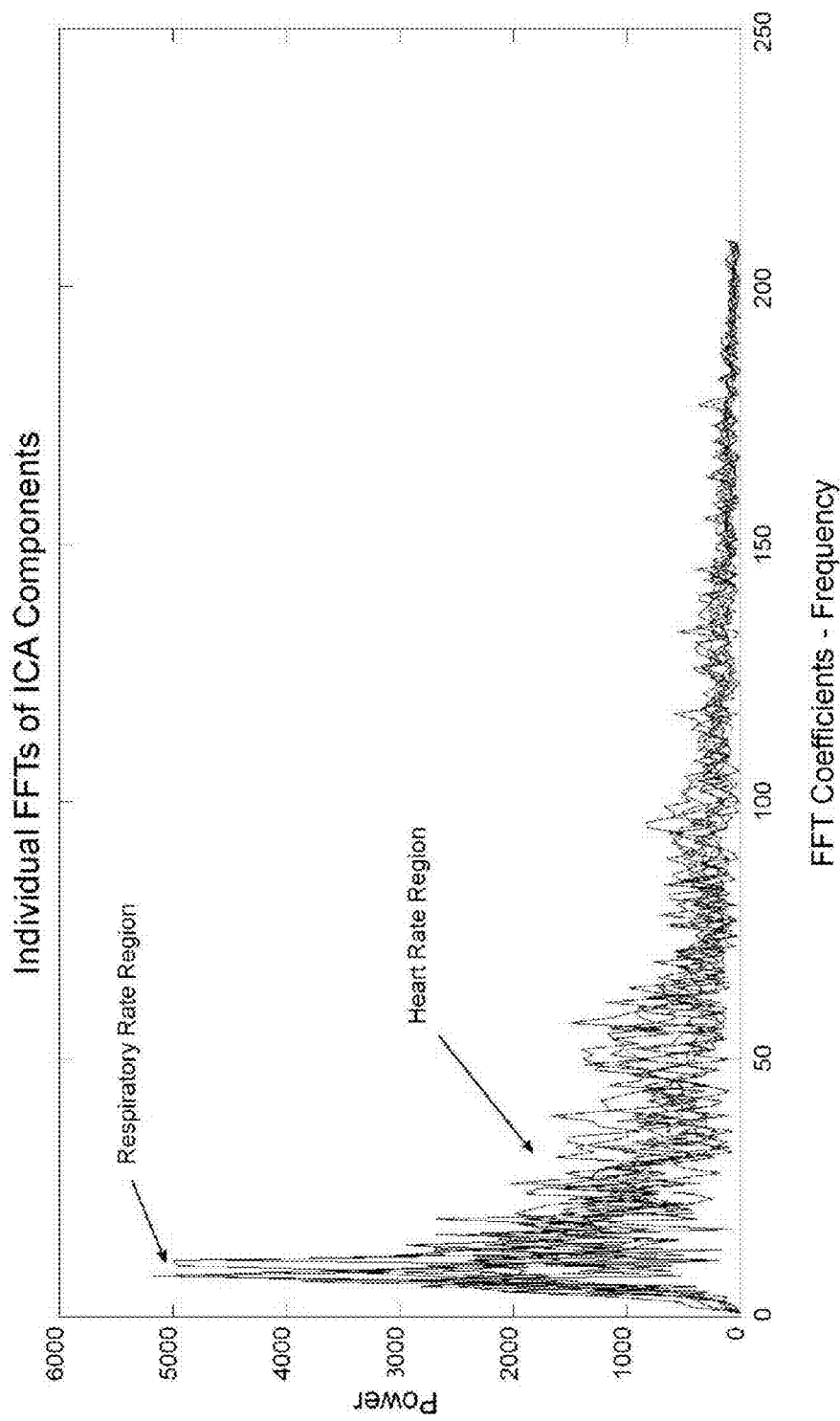
FIG. 22B illustrates one embodiment of 1D FFT of individual frequencies of ICA components.

After applying signal processing techniques for noise removal and signal conditioning (FIG. 21C) and initial signal processing in order to extract important features of the rhythm data (PCA and ICA: FIGS. 21D-F), the frequency analysis is done in order to determine the dominant frequencies, which will represent frequencies related to respiratory and heart rates. FIG. 22A presents two-dimensional FFT analysis results of all eight ICA components. The rhythm data presented is collected from a horse for about 7.5 minutes. Thus, the respiratory rate region and heart rate region are shown in FIG. 22A around 6 beats per minute ("BPM") and 30 BPM. The frequency scale in the figures is converted to BPM for better visual presentation. Similarly, FIG. 22B illustrates the frequency analysis of individual ICA components using one-dimensional FFT. Respiratory and heart rate regions are marked in all Figures.

Figure 22C:
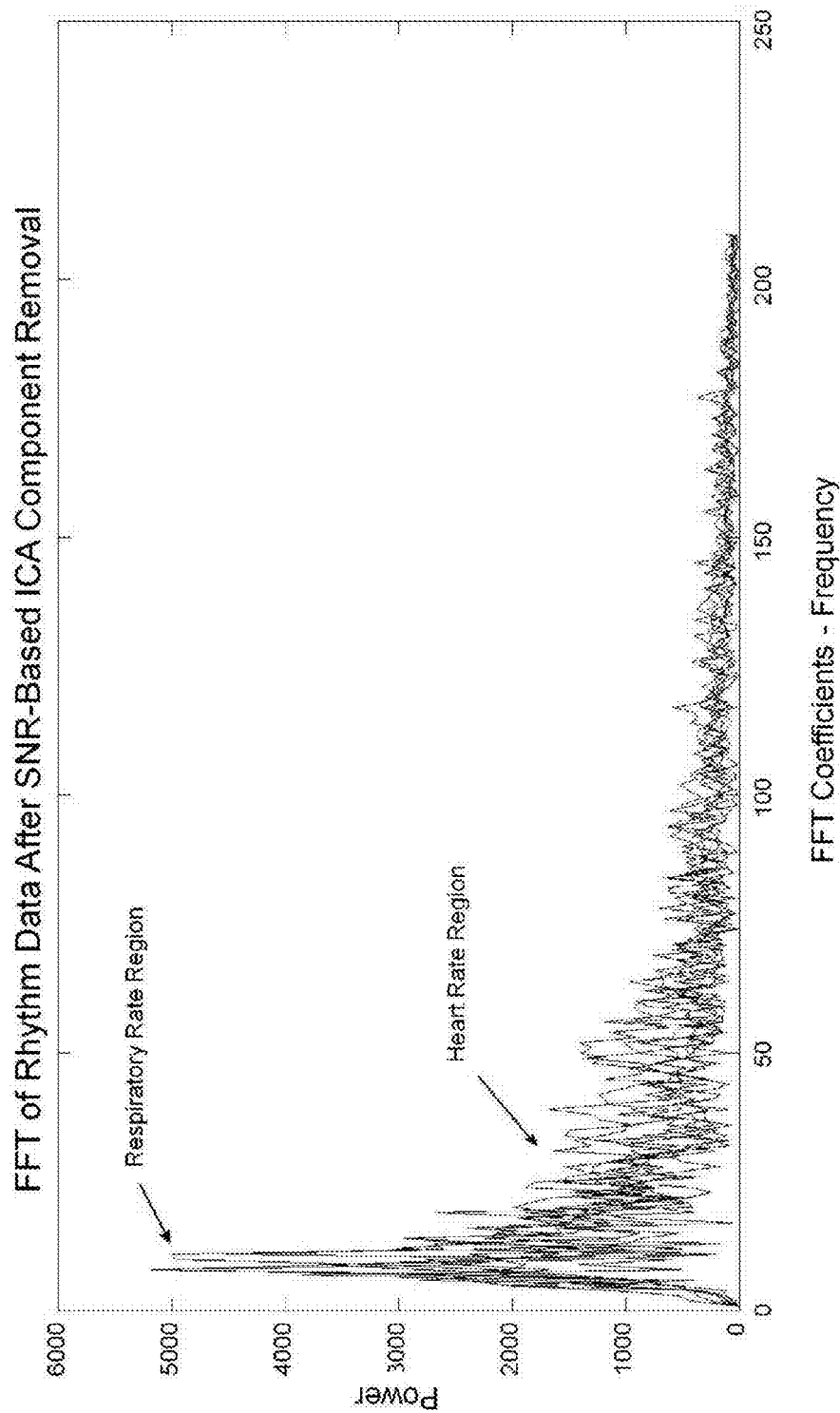
FIG. 22C illustrates one embodiment of FFT of rhythm data after SNR-based ICA component removal.
Figure 22D:
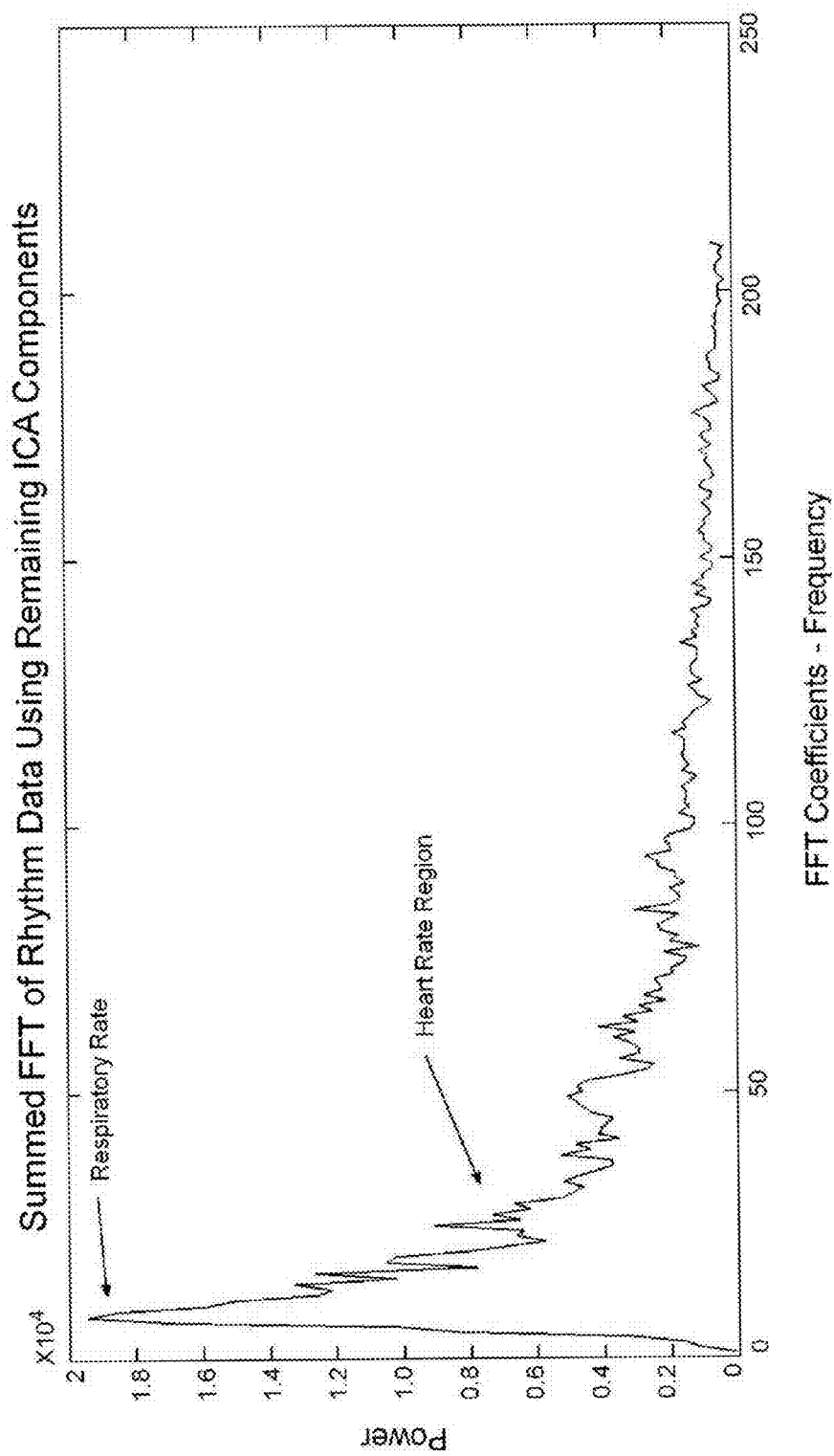
FIG. 22D illustrates one embodiment of FFT of rhythm data after summing FFT coefficients of ICA components.

The ICA analysis provides independent components of a signal in a compact form. However, depending on the number of independent components, the ICA components may have similar information and/or assign noise elements to one or more ICA components. Thus, by analyzing the ICA components with respect to noise content (i.e., signal to noise ratio ["SNR"]) can reveal the ICA components that have more noise than signal. Thus, by removing the ICA component that has the lowest SNR, the number of ICA components can be reduced in order to have a more compact and relevant variable space for frequency analysis. We determine the SNR values of each ICA component by analyzing FFT of each ICA component. The ICA removal process can be repeated if there are ICA components that have very low SNR values. FIG. 22C represents frequency analysis of seven ICA components after removing the ICA component that has the lowest SNR value. As can be seen, the respiratory and heart rate regions became more visible after the removal process. As can be seen in FIG. 22C, all seven ICA components do not have the same frequency characteristics. Thus, it is not possible to determine the respiratory and heart rates from one or more of the ICA components. However, as the respiratory and heart rates are dominant signals in the rhythm data, we see high-power values around their frequencies. Thus, we sum power of each frequency over all ICA components and expect to see very high power values around respiratory and heart rate regions. FIG. 22D shows the resulting frequency analysis after summing the FFT coefficients of ICA components over each frequency. By finding the frequency that has the highest power the respiratory rate can be determined as marked in FIG. 22C.

Figure 23:
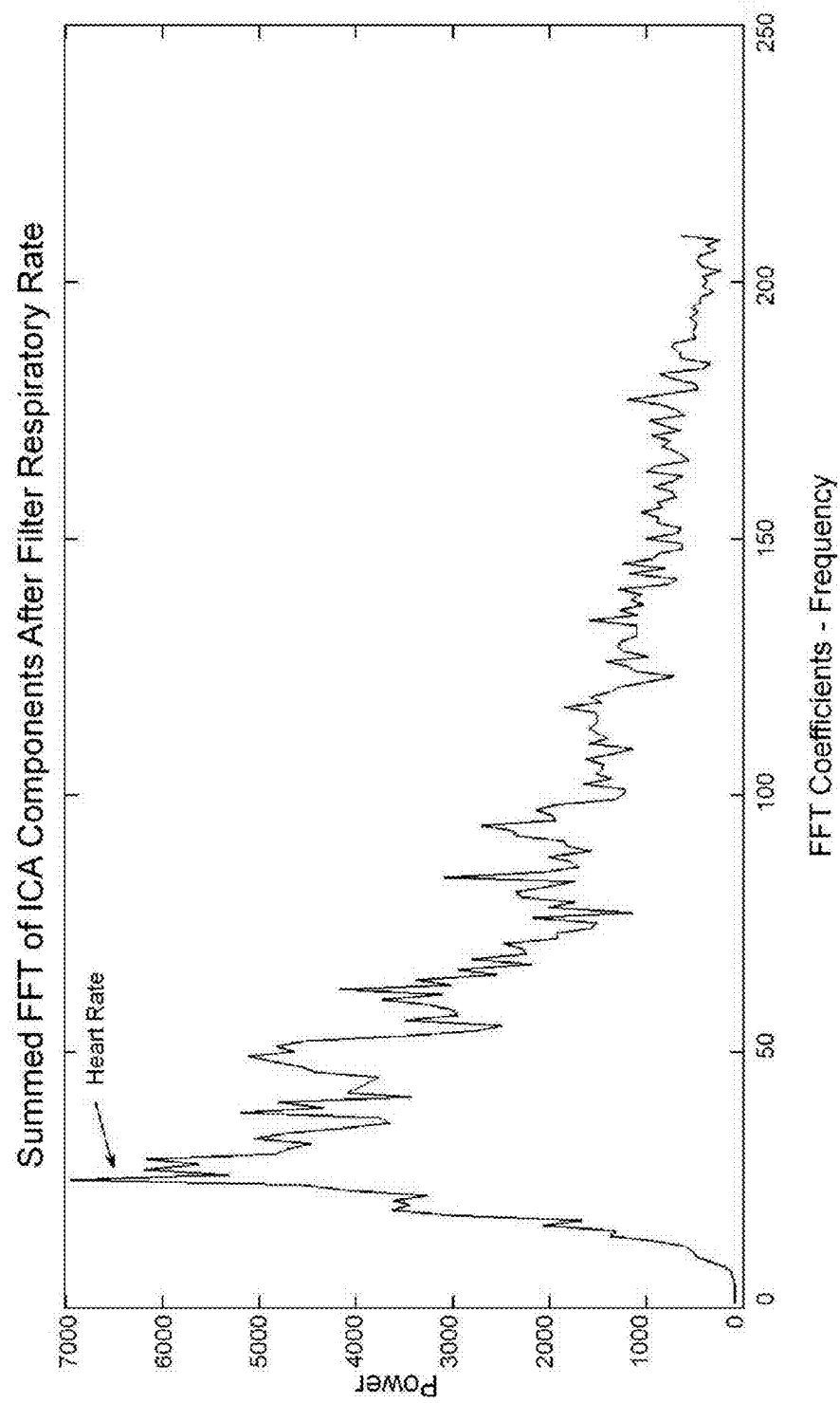
FIG. 23 illustrates one embodiment of summed FFT of ICA components after filtering of respiratory rate.

After determining the respiratory rate (i.e., frequency), a high-pass filter is applied so that frequencies around the respiratory rate are removed from the ICA components. FIG. 23 illustrates the frequency powers of the signal after filtering out the respiratory rate. Then, the heart rate is calculated by finding the frequency that has the highest power as depicted by the arrow in FIG. 23.

Real-Time Analysis/Determination

Figure 24:
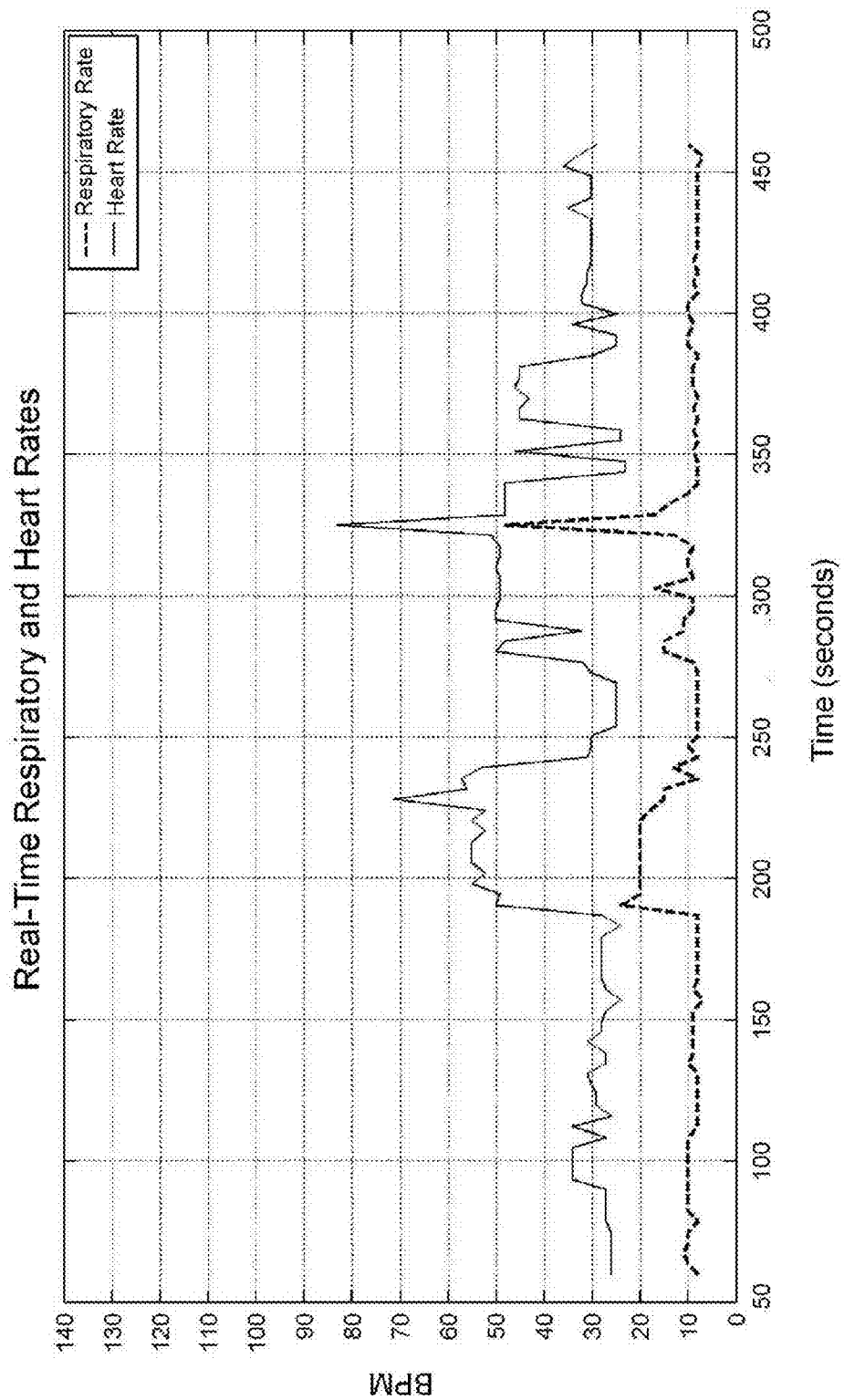
FIG. 24 illustrates one embodiment of real-time respiratory and heart rates for a horse over 7.5 minutes.
Figure 25:
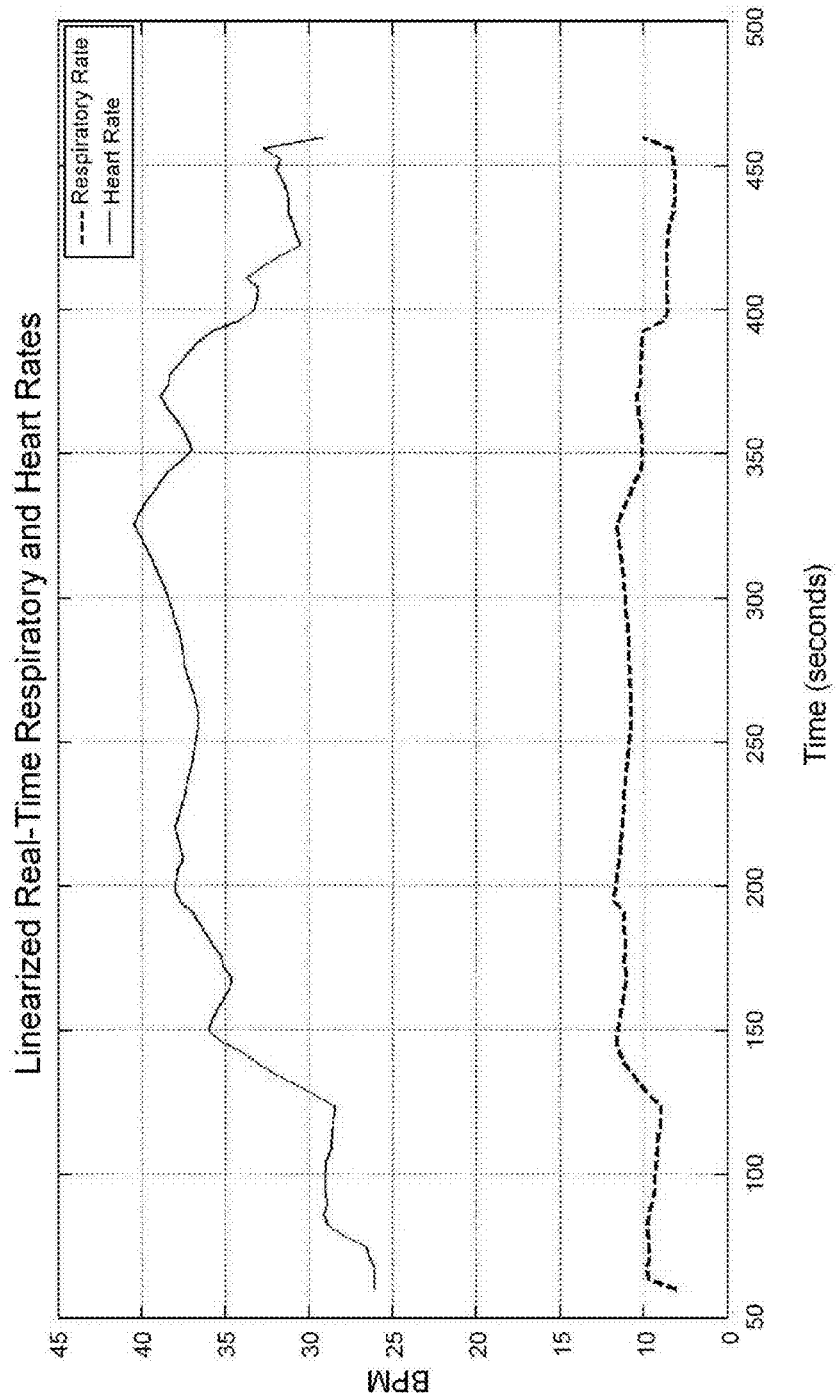
FIG. 25 illustrates one embodiment of linearized real-time respiratory and heart rates for a horse over 7.5 minutes.

As the UWB-IR provides a new reading every ~250 ms, the heart and respiratory rate algorithms can be applied to a window of a certain length (i.e., one minute). Then, the window can be shifted (i.e., 4 seconds) and the rates can be calculated again for that window. Thus, close to real-time analysis/determination of respiratory and heart rates is possible. FIG. 24 shows the real-time measurements of respiratory and heart rates for a horse for a duration of 7.5 minutes. As can be seen in FIG. 24, the rates can have some noise as the horse moves the equipment. Thus, a smoothing is needed to have a more stable reading of respiratory and heart rates for a horse, as shown in FIG. 25.

Biologic Algorithm

Figure 26:
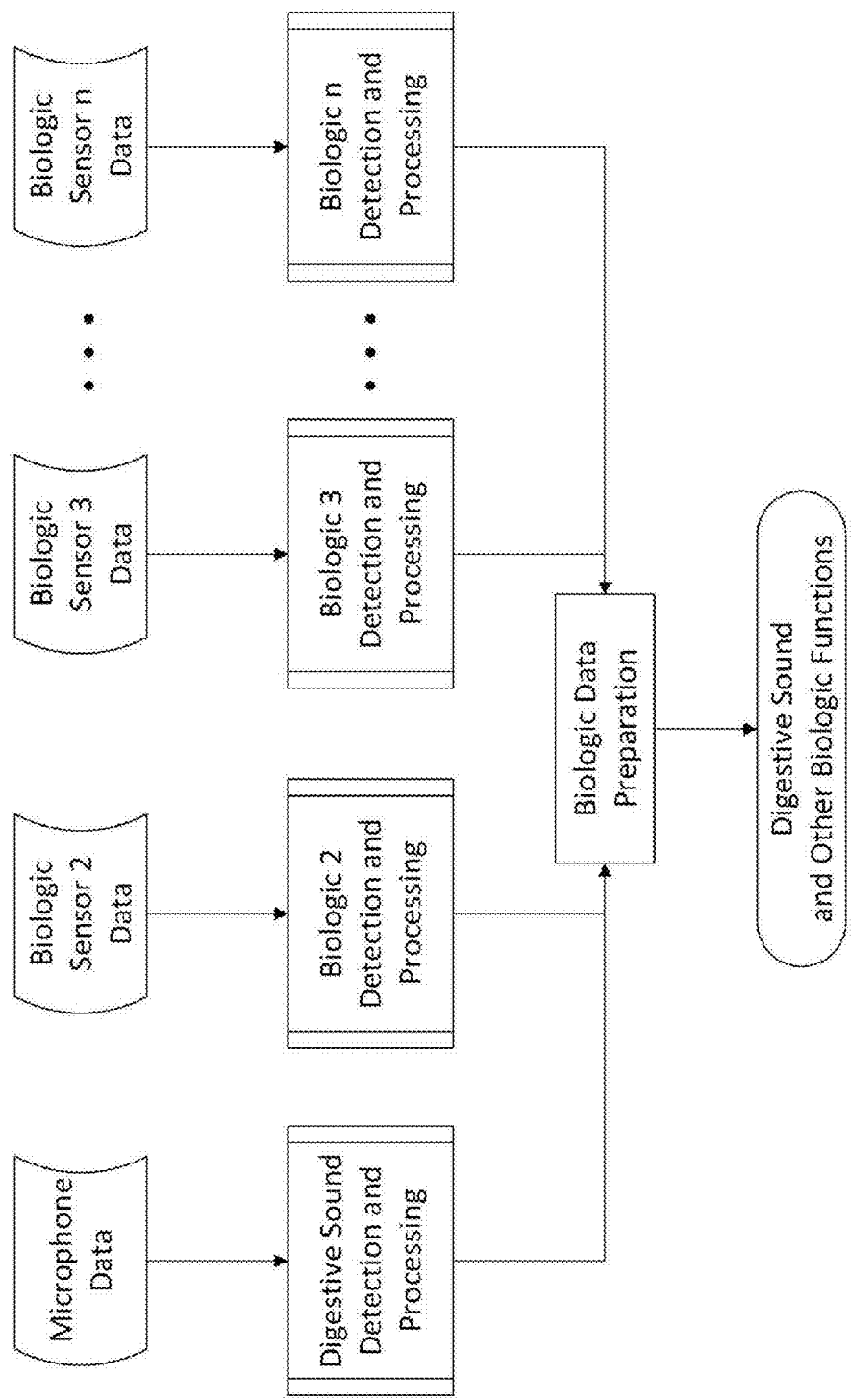
FIG. 26 illustrates one embodiment of a biologic algorithm.

With reference to FIG. 26, the biologic algorithm is a collection of signal detection and processing algorithms for determining biological data that is not a standard biometric. Biologics are values that describe non-specific anatomical condition/rate of an animal such as digestive/gut sounds. Thus, the main difference between biometric algorithm and biologic algorithm is that biometric algorithm is for standard biological metrics (biometric) that can be directly assessed.

Biologic sensors can be any sensors that are designed to provide data from an animal such as sound and perspiration (i.e., humidity of the skin). These sensors are not limited to sound and humidity; they can be expanded to collect other biological data as needed. For example in FIG. 26, a microphone is shown that senses the digestive/gut sounds and provides raw data for digestive sound detection and processing in or to qualify the digestive/gut sounds. This outputs the sound levels in decibels and their durations. Similarly, biologic detection and processing is need for each possible biologic sensor in the system. All the obtained biologic rate/condition feed the biologic data preparation block where these values are prepared to be integrated into the MASNS decision making-protocol as depicted in FIG. 3.

Adaptive Modeling

All animals are different. Horses themselves can differ physiologically due to a multitude of factors including breed, sex, age, diet, and activity level. This scope of differences makes it very difficult to establish an ideal model for the prototypical healthy horse that is not experiencing undue distress. Accordingly, it is important to establish a program for the system being claimed that can be configured to the particular individual animal being monitored, instead of simply being configured for the proto-horse. By customizing the interpretation of the data being acquired to a single individual animal, the device can more precisely determine the state of that the animal, and thus more efficiently achieve its purpose. By tailoring the interpretation of data being gathered from a particular animal to that particular animal's tendencies, the device is able to minimize the possibility of false positives and increase the likelihood of true positives.

The MASNS maintains a historical record of past sensor data for each individual animal, which—after a specified period of time—can be fed back into the data analysis system in order to tailor acceptable limits of the various data parameters being monitored. The MASNS may achieve this adaptation and conformity by manually or automatically updating the acceptable limits of various data parameters being monitored to take into account the historical record of past sensor data. In such an embodiment—after a specified period of time—the historical record of past sensor data will be assumed to be representative of the animal's non-stressed state unless otherwise indicated by a user.

Location/Position Sensors

Colic, along with other dangerous equine conditions, requires immediate attention when suspected. Time to intervention for diagnosis and treatment has a direct impact on that animal's outcomes. Often horses are located within large pastures, which can be very dark at night, and their exact location at any given time is unknown. Further many horses are transported for performance competitions, often hundreds of miles from home on commercial carriers, and their whereabouts is approximate at best to the animals' trainers, owners, and caretakers. Both scenarios can prove dangerous because when a horse is experiencing stress from colic or other conditions, it is of the upmost importance that they be treated as soon as possible.

Not only does this MASNS device assist in the early detection of colic, but the device also has an integrated location/positioning system along with the use of Wi-Fi and/or cellular signal strength triangulation to pinpoint the exact location of the distressed animal wearing the device so that treatment may be administered as soon as possible. Once the device has registered a positive state—indicating that the animal wearing the device may be in a distressed state—it activates the integrated location/positioning systems and transmits real-time data regarding the exact location/position of the animal in question to the caretaker via a wireless network. By assisting in rapid detection and treatment of the animal's condition, the MASNS device is able to provide the animal with the greatest chance of recovery and survival.

Power Management

Power management of the MASNS is critical for long-term use and low maintenance operation of the system. The remote MASNS device may remain active for a set period of time and then shut itself off. In one embodiment, the device may use small, high-capacity, high density, low self-discharge rechargeable batteries, such as, or similar to, lithium-polymer ("LiPo") batteries. These batteries allow the device to sit idle for hours, days, or even months without losing significant battery charge. A fixture/cradle capable of near-field induction charging may be utilized for replenishing power to batteries of MASNS device. Alternatively, or additionally, a direct connection comprised of electrically-conductive contacts may be utilized for recharging of batteries. In another embodiment, the device may use a renewable energy harvesting system (e.g., solar power, thermal energy, wind energy, kinetic energy) as a source of power.

Wireless data transmission can be carefully managed to conserve power. Algorithms in the processing unit may be used to associate vital signs, biologic functions, and animal posture and actions/motions with specific behaviors of interest. With course analysis being performed by the algorithms at the point-of-care (i.e., at the level of the animal) and refined analysis, where warranted, is performed by off-site central computer/station, power and energy is conserved by eliminating the need to transmit all input data from sensors for analysis. Rather, through point-of-care analysis, transmission of data occurs only when certain states or actions, such as possible distress behaviors, are detected.

Point-of-Care Analysis

The system being claimed is constantly monitoring the animal that is wearing the MASNS device in order to provide the most thorough and accurate determination of the animal's condition at any given point in time. To be able to do this, the device requires a power source. While operating all of the sensors integrated into the device takes some power, one of the activities of the system that consumes a large amount of power is the transmission of data to an external source. Due to the high power cost of external data transmission, the device may have the data processing unit integrated into the device itself. If the data processing unit is contained within the device itself the need to regularly transmit large quantities of data to an external source for analysis is removed. Accordingly, in an embodiment having integrated data analysis unit, the device would only need to transmit information to an external source when actively alerting the caretaker of a positive reading of distress or when actively queried by an outside source. By integrating the data processing unit into the device itself and not having it in an external off-site system, the device can minimize the amount of time and data that must be transmitted externally, thus minimizing power consumption and extending the single charge operating life of the system.

Additionally, integrating the data analysis hardware into the device itself allows for the data analysis means to be dedicated to the interpretation of data from just the one animal that the particular device is monitoring. If an external off-site data analysis means is being used, it is likely not dedicated to monitoring a single animal, but rather aggregate monitoring a multitude of animals simultaneously. Furthermore, coupling the system's data analysis means with adaptive algorithms, and then limiting the data acquisition and analysis to an individual animal allows for the customization of variable threshold values for a particular animal under surveillance by a particular MASNS device. This results in the system functioning more accurately and efficiently over time.

The processing unit may be configured to have a sleep mode and a wake-on-signal operation. In one embodiment the processing unit may be in sleep mode most of the time, requiring little power. The processing unit may then respond to any predetermined parameters that are programmed into it by waking and beginning operation when the predetermined parameters are met. This sleep/wake loop may be, but is not limited to being, event or time driven. In one embodiment, the instant-wake time stamp is compared with the previous time stamp from the last sleep; if the time difference is not within a designated time period, the time stamp is set to the current time, the sensors are deactivated, and the sensor unit is put back into sleep mode. This power management loop can essentially be a coarse false-alarm check.

Each physiologic value and characteristic behavior, evaluated independently or together, may be an indicator or a counter-indicator of a distress condition. Positive equine biometric distress indicators may include an elevation of heart rate >40 beats per minute, increase in respiratory rates >16 breaths per minute, and/or rising of the horse's core body temperatures >100.4 degrees Fahrenheit. Counter equine biometric distress indicators may include an oscillating heart rate of 30-40 beats per minute, respiratory rates of 8-16 breaths per minute, and/or core body temperatures of 98.6-100.4 degrees Fahrenheit.

Positive equine motion distress indicators may include repeated episodes of rising/falling with high activity over an extended time period while the horse is lying down (i.e., rolling+/−thrashing of legs), nipping at sides, etc. Counter equine distress indicators may include a full-body "healthy shake" upon standing/rising after rolling and minimal activity while the horse is lying down.

Data Transmission Networks

Horses and other farm-type animals are often kept and allowed to roam on large tracts of rural land. On such expansive tracts, it is unlikely that there is the infrastructure present for wireless network coverage.

In one embodiment, the MASNS device incorporates transceivers that are compatible with use on a wireless network. Alternatively, or additionally, in other embodiments the MASNS device incorporates transceivers that operate on other mobile wireless (electromagnetic) systems including, but not limited to 3G networks, 4G networks, Wi-Fi networks (standard and long-range networks), mesh networks, and other wireless data transmission systems.

The use of transceivers compatible with these different wireless networks may give the device the ability to transmit and receive transmissions from a broad range of devices over a potentially broader area of land coverage than what standard Wi-Fi can offer. When environmental conditions or the accessibility or cost to connect with a cellular network is of concern a base station may be utilized. This base station will allow multiple MASNS devices to access a single internet connection provided by user/facility. This is of particular importance given the rural, remote, and undeveloped nature of locations where many horses and other animals tend to be located.

Bidirectional Communications and Interactions

In one embodiment, the MASNS may contain not only a data transmitter for sending the caretaker alerts when the device determines the animal being monitored may be experiencing sufficient stress (so as to require assistance), but may also contain a wireless receiver. Incorporating a wireless receiver into the system allows for bidirectional interaction, which facilitates the exchange of data between the MASNS device and external sources. Not only would the system be able to push alerts to the caretaker, but the caretaker would be able to actively query the MASNS for any number of reasons. The user could send a signal to the receiver incorporated into the MASNS triggering the system to respond with the current status of the monitored animal, including real-time readouts of any/all of the data being collected.

The incorporation of a wireless receiver into the MASNS would not only allow the caretaker to remotely access information the system is gathering in real-time, but may also allow for the caretaker to check on the operational status of the MASNS itself from a remote location. This feature would save the caretaker time, energy, and resources by abolishing the process of tracking down the animal under surveillance and physically inspecting the MASNS in order to determine its operational status. Such operational status and other MASNS calibration techniques can be enhanced by multi-sensory indicators/actuators (e.g., LED lights, vibrators, buzzers). In another embodiment such indicators/actuators can be incorporated and utilized for Pavlovian conditioning, negative feedback, and blocking.

Data Display

In one embodiment, the information (including real-time data) gathered by the MASNS can be streamed, or otherwise transmitted to, and displayed on, a remote device. At any time the user may query the MASNS through the wireless network. Once queried, the MASNS can transmit records of the data parameters monitored by the MASNS to user's remote device, including but not limited to, a computer, a tablet, and a smart phone. This feature allows a user to conveniently check on the status of any animal being monitored in a real-time fashion from a remote location, without the need for specialized hardware.

Additionally, this feature will work synergistically with both the use of data transmission through mobile networks and with the aforementioned location/positioning system(s) included in the device. By allowing the information gathered to be in a format that can be displayed on devices that already utilize mobile wireless networks there will be no need for the user to buy specialized hardware in order to remotely monitor the animals. Furthermore, by allowing the caretaker to use a portable device, such as a smart phone, to link with the location/positioning function included in the device, said caretaker may easily receive updates with the real-time location of the animal being monitored while the caretaker is on the move.

While specific embodiments and applications have been illustrated and described, it is to be understood that the current disclosure is not limited to the precise configuration and components disclosed herein. Various modifications, changes, and variations apparent to those of skill in the art may be made in the arrangement, operation, and details of the device and methods of the present invention disclosed herein without departing from the spirit, scope, and underlying principles of the disclosure.

What is claimed is:

1. A method for detecting one or more biometric parameter in an animal comprising:
    using ultra-wide band impulse radar (UWB-IR) to acquire one or more of respiratory rhythm data and cardiac rhythm data of the animal;
    determine a time-based motion by collecting most current raw motion data;
    preprocessing the one or more of respiratory rhythm data and cardiac rhythm data to remove noise resulting from movement of the animal by filtering the time-based motion;
    differentiating between the one or more of respiratory rhythm data and cardiac rhythm data by feature reduction and extraction through conditioning of acquired rhythm data;
    using fast Fourier transform for frequency analysis of the conditioned rhythm data to determine a power level of respective dominant frequencies which represent frequencies related to the one or more of respiratory rate and heart rate; and
    determining one of a respiratory rate and a heart rate of the animal by correlating the respective dominant frequencies with a respective one of a respiratory signal and a cardiac signal of the animal.

2. The method of claim 1, further comprising determining when one or more of a respiratory rate and a cardiac rate of the animal exceeds one or more of a predefined threshold and historical threshold indicative of the possible distress in the animal.

3. The method of claim 2, further comprising notifying one or more remote caretakers of the possible distress in the animal based on the determining.

4. The method of claim 2, further comprising continuously personalizing a range of predefined thresholds to conform to the least one of respiratory rate data and heart rate data specific to the animal over time.

5. The method of claim 3, wherein notifying one or more caretakers comprises activation of an escalating notification protocol across multiple channels.

6. The method of claim 1, further comprising using the least one of respiratory rate data and heart rate data to detect onset of foaling.

7. A method for mobile, point-of-care equine surveillance and distress monitoring in an animal comprising:
    monitoring at least one of a respiratory rate and a heart rate of an animal using UWB-IR to acquire at least one of respiratory rate data and heart rate data;
    determine a time-based motion by collecting most current raw motion data;
    preprocessing the at least one of respiratory rate data and heart rate data to remove noise resulting from movement of the animal by filtering the time-based motion;
    monitoring the temperature of an animal using a thermal infrared sensor;
    monitoring the behavior of the animal using at least one of an accelerometer, gyroscope, magnetometer, and barometric pressure sensor;
    determining the posture and location of the animal using at least one of a barometric pressure sensor, global positioning system sensor, and Wi-Fi triangulation;
    determining when at least one parameter of the respiratory rate, heart rate, temperature, behavior, and posture of the animal exceeds a single threshold value;
    determining, using a one-class classifier, when a combination of parameters of the respiratory rate, heart rate, temperature, behavior, and posture of the animal exceeds a threshold value indicative of possible distress in the animal; and
    activating an escalating notification protocol across multiple channels to inform one or more remote caretakers of the possible distress in the animal.

8. The method of claim 7, further comprising detecting one or more biologic function parameter of the animal.

9. The method of claim 8, further comprising monitoring digestive activity of the animal using a microphone.

10. The method of claim 8, further comprising:
    detecting one or more novel events though use of a one-class classifier when the one or more detected biologic function parameter falls outside one or more of predefined personalized historical parameter value ranges for the animal; and
    continuously updating a range of at least one of predefined biologic function parameter values, single threshold values, and composite threshold values to conform to the one or more detected biologic function parameter specific to the animal over time.

11. The method of claim 7, further comprising determining occurrence of one or more novel events though use of a one-class classifier when one or more detected parameters fall outside one or more of predefined personalized historical parameter value ranges for the animal.

12. The method of claim 7, further comprising continuously updating a range of at least one of predefined parameter values, single threshold values, and composite threshold values to conform to detected parameters for specific to the animal over time.

13. The method of claim 7, further comprising sending a notification when one or more of the heart rate, respiratory rate, and temperature is outside an adaptively-derived empirical upper limit of normal and lower limit of normal for the animal while at rest.

14. The method of 13, further comprising:
    generating one or more of a first watch notification when the heart rate is greater than about 15% above the resting normal (RN) or is greater than about 15% below the RN for a period of time, a second warning notification when the heart rate is greater than about 40% above the RN or is greater than about 40% below RN for a period of time, and a third alert notification when the heart rate is greater than about 70% above the RN or is greater than about 70% below RN for a period of time;
    generating one or more of the first watch notification when the respiratory rate is greater than about 35% above the RN or is greater than about 35% below RN for a period of time, the second warning notification when the respiratory rate is greater than about 75% above the RN or is greater than about 50% below the RN for a period of time, and the third alert notification when the respiratory rate is greater than about 150% above the RN or is greater than about 65% below the RN for a period of time; and generating one or more of the first watch notification when the temperature is greater than about 1% above the RN or is greater than about 1% below the RN for a period of time, the second warning notification when the temperature is greater than about 2% above the RN or is greater than about 1.75% below the RN for a period of time, and the third alert notification when the temperature is greater than about 4% above the RN or is greater than about 3.5% below the RN for a period of time.

15. The method of claim 7, further comprising detecting one or more behavioral parameters of the animal by monitoring data from one or more of an accelerometer, gyroscope, magnetometer, and barometric pressure sensor.

16. The method of claim 15, further comprising using the at least one of respiratory rate data, heart rate data, and behavioral parameter data to detect distress in the animal.

17. The method of claim 7, further comprising using the least one of respiratory rate data and heart rate data to detect onset of foaling.

18. The method of claim 13, wherein sending a notification to one or more caretakers comprises activation of an escalating notification protocol across multiple channels.

19. An electronic device comprising a processor for equine surveillance and monitoring of an animal:
the processor programmed to:
use ultra-wide band impulse radar (UWB-IR) to acquire one or more of respiratory rhythm data and cardiac rhythm data of the animal;
determine a time-based motion by collecting most current raw motion data;
preprocess the one or more of respiratory rhythm data and cardiac rhythm data to remove noise resulting from movement of the animal by filtering the time-based motion;
differentiate between the one or more of respiratory rhythm data and the cardiac rhythm data by feature reduction and extraction through conditioning of acquired rhythm data;
use fast Fourier transform for frequency analysis of the conditioned rhythm data to determine a power level of respective dominant frequencies which represent frequencies related to the one more of respiratory rate and heart rate; and
determine one of a respiratory rate and a heart rate of the animal by correlating the respective dominant frequencies with a respective one of a respiratory signal and a cardiac signal of the animal.

20. The device of claim 19, wherein the processor is further programmed to use the least one of respiratory rate data and heart rate data to detect onset of foaling.

* * * * *